(12) United States Patent
Chai et al.

(10) Patent No.: US 9,938,415 B2
(45) Date of Patent: Apr. 10, 2018

(54) FUNCTIONALISED ANTIFOULING COMPOUNDS AND USE THEREOF

(71) Applicants: Agency for Science, Technology and Research, Singapore (SG); National University of Singapore, Singapore (SG); Maritime and Port Authority of Singapore, Singapore (SG)

(72) Inventors: Christina Li Lin Chai, Singapore (SG); Brendan Adrian Burkett, Singapore (SG); Serena Lay Ming Teo, Singapore (SG); Daniel Rittschof, Morehead City, NC (US); Serina Siew Chen Lee, Singapore (SG); Gary Howard Dickinson, Singapore (SG); Han Hong, Singapore (SG)

(73) Assignees: Agency for Science, Technology and Research, Singapore (SG); National University of Singapore, Singapore (SG); Maritime and Port Authority of Singapore, Singapore (SG)

( * ) Notice: Subject to any disclaimer, the term of this patent is extended or adjusted under 35 U.S.C. 154(b) by 0 days.

(21) Appl. No.: 14/859,935

(22) Filed: Sep. 21, 2015

(65) Prior Publication Data
US 2016/0009926 A1     Jan. 14, 2016

Related U.S. Application Data

(63) Continuation of application No. 13/576,808, filed as application No. PCT/SG2011/000052 on Feb. 2, 2011, now Pat. No. 9,169,223.
(Continued)

(51) Int. Cl.
*C09D 5/16* (2006.01)
*C07C 235/34* (2006.01)
(Continued)

(52) U.S. Cl.
CPC ........... *C09D 5/1668* (2013.01); *A01N 25/10* (2013.01); *A01N 37/18* (2013.01); *C07C 233/11* (2013.01);
(Continued)

(58) Field of Classification Search
CPC .................................................... C09D 5/1668
See application file for complete search history.

(56) References Cited

U.S. PATENT DOCUMENTS 5,990,043 A  11/1999 Kugler et al.
6,245,784 B1  6/2001 Kugler et al.
(Continued)

FOREIGN PATENT DOCUMENTS

FR    2068439 A6   8/1971
FR    2659968 A1   9/1991
(Continued)

OTHER PUBLICATIONS

Hama, Palladium-Catalyzed Intermolecular r-Arylation of Zinc Amide Enolates under Mild Conditions, J. Am. Chem. Soc., 2006, 128, 4976-4985.*
(Continued)

*Primary Examiner* — Paul W Dickinson
(74) *Attorney, Agent, or Firm* — Choate, Hall & Stewart LLP; Charles E. Lyon; Kristen C. Buteau

(57) ABSTRACT

The present invention relates to derivatives of α, α-disubstituted amide compounds which comprise a substituted aryl at the α carbon such that the substituent provides a means for attachment or incorporation of the compound to or in a polymer. The provision of such a substituent on the aryl has surprisingly been found not only to permit attachment to or incorporation n a polymer but also retention of useful antifouling activity. In embodiments, the substituent is selected from hydroxyl, ethers, esters, carboxyls, alkylsilyls
(Continued)

and alkenyls. Experiments demonstrate that antifouling activity can be as good or better as the corresponding unsubstituted compound and that polymers functionalized so as to include or be formed from the substituted compound can be used to reduce settlement.

19 Claims, 1 Drawing Sheet

Related U.S. Application Data

(60) Provisional application No. 61/300,509, filed on Feb. 2, 2010.

(51) Int. Cl.
| | |
|---|---|
| C07D 295/185 | (2006.01) |
| A01N 25/10 | (2006.01) |
| A01N 37/18 | (2006.01) |
| C07C 233/11 | (2006.01) |
| C07D 295/192 | (2006.01) |
| C08F 120/34 | (2006.01) |
| C09D 5/14 | (2006.01) |

(52) U.S. Cl.
CPC ........ *C07C 235/34* (2013.01); *C07D 295/185* (2013.01); *C07D 295/192* (2013.01); *C08F 120/34* (2013.01); *C09D 5/165* (2013.01); *C09D 5/1625* (2013.01); *C09D 5/14* (2013.01)

(56) References Cited

U.S. PATENT DOCUMENTS

| | | |
|---|---|---|
| 6,627,675 B1 | 9/2003 | Finnie et al. |
| 6,692,557 B1 | 2/2004 | De Nys et al. |
| 6,929,685 B2 | 8/2005 | Bernard et al. |
| 9,169,223 B2 | 10/2015 | Chai et al. |
| 2012/0301423 A1 | 11/2012 | Chai et al. |

FOREIGN PATENT DOCUMENTS

| | | | |
|---|---|---|---|
| JP | 52007053 B | 2/1977 | |
| JP | 2002272993 A | 9/2002 | |
| JP | 5200705 B2 | 6/2013 | |
| WO | WO-97/11910 A1 | 4/1997 | |
| WO | WO-2003/084941 A2 | 10/2003 | |
| WO | WO-2005/037279 A1 | 4/2005 | |
| WO | WO 2008093142 A1 * | 8/2008 | ........... C07C 213/02 |
| WO | WO-2008/130558 A2 | 10/2008 | |
| WO | WO-2009/139729 A1 | 11/2009 | |

OTHER PUBLICATIONS

Bellas et al., Effects of medetomidine, a novel antifouling agent, on the burrowing bivalve Abranitida (Muller), Chemosphere, 65: 575-582, 2006.
Bellas, Juan, Toxicity of the booster biocide Sea-Nine to the early developmental stages of the sea urchin *Paracentrotus lividus*, Aquatic Toxicology, 83: 52-61, 2007.
CAS Registry File RNs, [234446-91-4] and [234446-92-5], STN Entry Date—Aug. 24, 1999.
Chelossi et al., Comparative assessment of antimicrobial efficacy of new potential biocides for treatment of cooling and ballast waters, Science of the Total Environment, 356: 1-10, 2006.
Chemical Abstracts. Accession No. 1972:405169 (Oct. 1971).
Chemical Abstracts. Accession No. 1983: 197699 & Hamacher et al., Potential antineoplastics. VI. Synthesis of hexestrol derivatives with alkylated side chains Archive der Pharmazie, 316(3), pp. 271-281 (1983).
Chemical Abstracts. Accession No. 1992:106277 (Sep. 1991).
Choong et al., A Preliminary Ecotoxicity Study of Pharmaceuticals in the Marine Environment, Journal of Toxicology and Environmental Health, Part A, 69(21): 1959-1970, 2006.
Feng et al., Pyrethroids as Promising Marine Antifoulants: Laboratory and Field Studies, Mar Biotechnol, 11: 153-160, 2009.
Hama et al., Palladium-Catalyzed Intermolecular a-Arylation of Zinc Amide Enolates under Mild Conditions, J. Am. Chem. Soc., 128: 4976-4985, 2006.
Harino et al., Concentrations of Antifouling Biocides in Sediment and Mussel Samples Collected from Otsuchi Bay, Japan, Arch. Environ. Contam. Toxicol., 52: 179-188, 2007.
Hoye et al., Total Syntheses of Korupensamine C and Ancistrobrevine B, Tetrahedron Letters, 37(18): 3097-3098, 1996.
Hoye et al., Total Synthesis of Michellamines A-C, Korupensamines A-D, and Ancistrobrevine B, J. Org. Chem. 64: 7184-7201, 1999.
International Preliminary Report on Patentability for PCT/SG11/000052, dated Jan. 9, 2012.
Janser et al., A cassette-dosing approach for improvement of oral bioavailability of dual TACE/MMP inhibitors, Bioorganic & Medical Chemistry Letters, 16: 2632-2636, 2006.
Kem et al., Inhibition of barnacle larval settlement and crustacean toxicity of some hoplonemertine pyridyl alkaloids, Biomolecular Engineering, 20: 355-361, 2003.
Konstantinou et al., Worldwide occurrence and effects of antifouling paint booster biocides in the aquatic environment: a review, Environmental International, 30: 235-248, 2004.
Pitombo, F. B., Phylogenetic analysis of the Balanidae (Cirripedia, Balanomorpha). Zool. Scr. 33: 261-276 (2004).
Rittschof et al., Barnacle in vitro assays for biologically active substances: Toxicity and Settlement inhibition assays using mass cultured Balanus amphitrite amphitrite darwin, Biofouling, 6(2): 115-122, 1992.
Rittschof et al., Pharmaceuticals as antifoulants: Concept and principles, Biofouling, 19(1): 207-212, 2003.
Rittschof et al., Settlement and behavior in relation to flow and surface in larval barnacles, Balanus amphitrite Darwin' J. Exp. Mar. Biol. Ecol. 82, 131-146 (1984).
Vicario et al., A New General Method for the Asymmetric Synthesis of 4-Alkyl-3-aryl-1,2,3,4-tetrahydroisoquinolines, J. Org. Chem. 64: 4610-4616, 1999.
Vicario et al., The first stereocontrolled synthesis of 12-methyl-hexahydrobenzo[c]phenanthridine alkaloids, Tetrahedron: Asymmetry, 10: 1947-1959, 1999.
Viteva et al., Effect of Electronic and Steric Factors on Stereochemistry of Michael Reaction Between N, N-Dimethylarylacetamides and Methyl Cinnamate, Doklady Bolgarskoi Akademii Nauk, 35(8): 1077-1080, 1982.
Voulvoulis et al., Antifouling Paint Booster Biocides: Occurrence and Partitioning in Water and Sediments, Hdb Env Chem, 5(0): 155-170, 2006.
Watanabe et al., Reaction of Lithiated Senocioamide and Related Compounds with Benzynes: Efficient Syntheses of Naphthols and Naphthoquinones, Chem. Pharm. Bull., 34(7): 2810-2820, 1986.
Written Opinion for PCT/SG11/000052, dated Apr. 5, 2011.
Yamashita et al., An Improved Assay Method for Antifouling Substances Using the Blue Mussel, *Mytilus edulis*, Agric. Biol. Chem., 53(12): 3319-3321, 1989.
Yamashita et al., Isolation of Nicotinamide from Mallotus Leaves as an Attaching Repellent against the Blue Mussel, *Mytilus edulis*, Agric. Biol. Chem., 53(12): 3351-3352, 1989.
Zigterman et al., Highly Selective Rhodium-Catalyzed Conjugate Addition Reactions of 4-Oxobutenamides, J. Org. Chem., 72: 8870-8876, 2007.

* cited by examiner

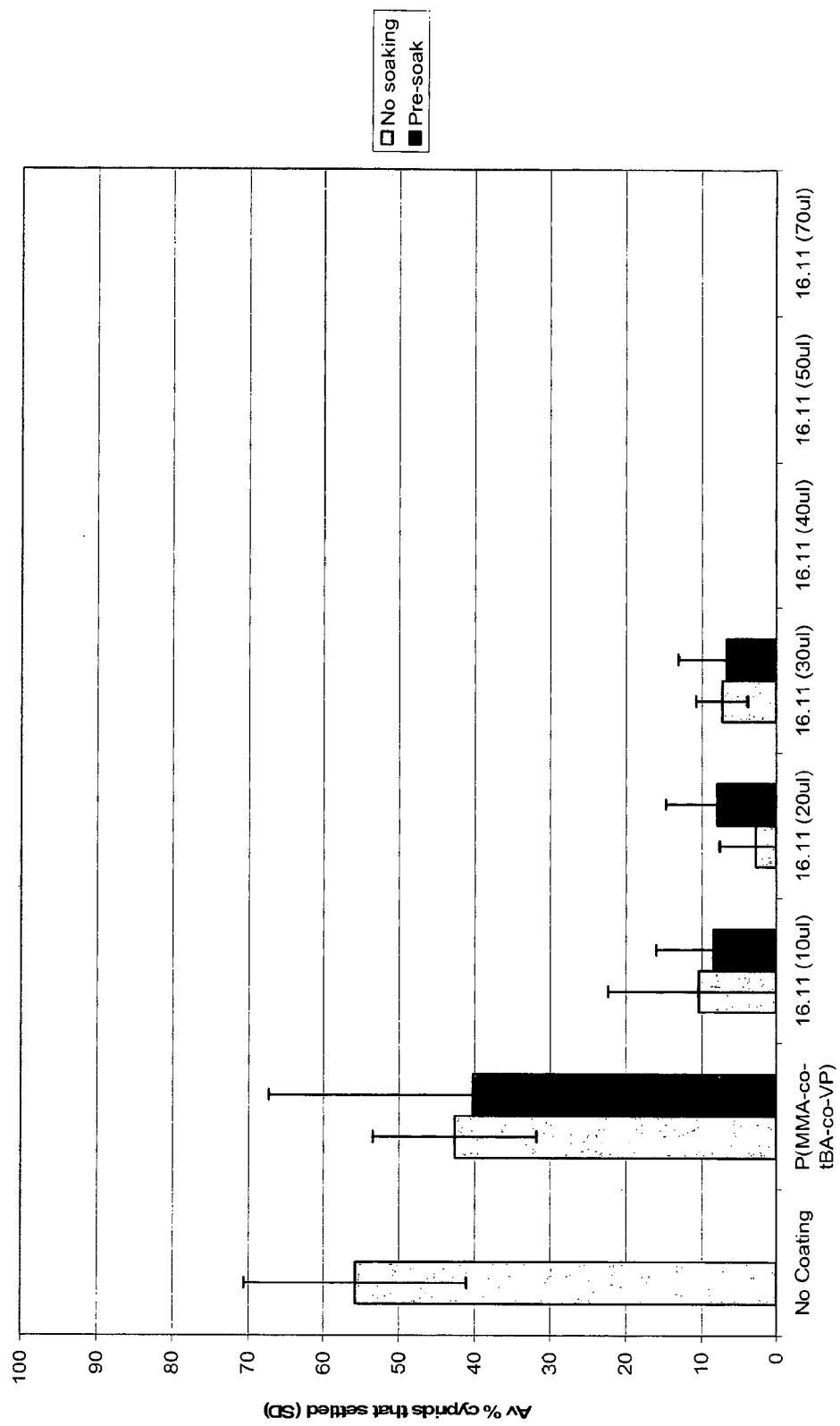

FUNCTIONALISED ANTIFOULING COMPOUNDS AND USE THEREOF

FIELD OF THE INVENTION

The present invention is concerned with small functionalised amide molecules that exhibit antifouling and/or antibacterial activity and their use in the control of bacterial films and organism growth in the marine environment.

BACKGROUND

Marine fouling refers to the settlement and growth of organisms on submerged, manufactured surfaces and has been has been a problem since the dawn of maritime history. Colonization of submerged surfaces by marine organisms occurs within days to weeks of the surface entering the marine environment and, given the ever-increasing presence of maritime structures (underwater cables, generators, pipelines etc), the battle against fouling organisms is becoming an increasingly significant challenge. The need for effective methods to control marine fouling is of paramount importance to the international shipping industry.

Antifouling coatings prevent the settlement of marine organisms, generally by killing larval foulers through the action of broad spectrum biocides such as organotin or copper compounds. Although extremely effective, environmental degradation resulting from the use of organotin compounds was so severe that marine paint companies voluntarily withdrew these paints from the market in 2003, and the IMO banned their use in 2008 (International Convention on the Control of Harmful Anti-fouling Systems on Ships, entered into force 17 Sep. 2008). Although copper and biocide booster containing paints are still widely available, their use is not desirable since they have the potential to accumulate in the marine environment (Voulvoulis, 2006).

Current commercial marine coatings can be divided into two classes: antifouling and foul-release. Antifouling coatings use broad-spectrum biocides which kill foulers by oxidation or, more usually, exposure to toxic metal ions. Foul-release coatings are mainly silicon based polymers that are easy to clean, however the best of these usually also contain additives and catalysts that kill organisms. As noted above, legislation and agreements, based on the recognition of the environmentally unacceptable consequences of toxic antifouling agents such as tributyl tin in coatings, have prompted interest to develop new less environmentally pernicious coatings.

An approach reported by Teo et al (an inventor of the present application) in U.S. Ser. No. 11/265,833, is the use of pharmaceuticals as antifouling agents. It has been demonstrated that pharmaceuticals may disrupt the metamorphosis of fouling organisms. Commercially available pharmaceuticals, with their known synthesis, chemical properties and primary mechanism of action in vertebrates and in humans, were screened as potential sources of antifouling agents. Whilst eight pharmaceuticals with promising bioactivity were reported, there remains the problem that these pharmaceuticals may accumulate in the marine environment. Furthermore, some of these pharmaceuticals suffer from delivery problems because of poor solubility in sea water.

A further alternative to broad spectrum biocides is small, biodegradable organic molecules that inhibit the settlement of marine organisms. Such molecules should not be recalcitrant in the environment and should be "benign by design".

To this end, Teo et al recently demonstrated the antifouling potential of a family of simple α,α-disubstituted amides (selected examples shown below) on larval barnacles and bacterial biofilms (PCT/SG2009/000175). These molecules are predicted to breakdown rapidly in the marine environment.

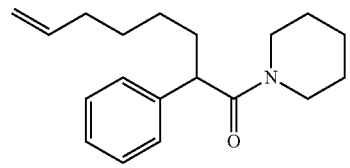

Barnacle Toxicity: 3 μg/mL
Anti-settlement: 0.47 μg/mL 12.4

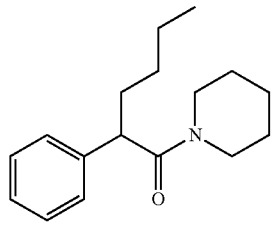

Barnacle Toxicity: 9.11 μg/mL
Anti-settlement: 1.50 μg/mL 12.1

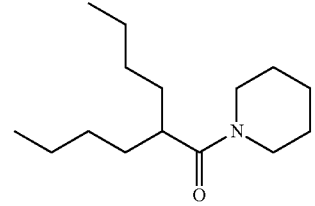

Barnacle Toxicity: 9.83 μg/mL
Anti-settlement: 2.00 μg/mL 12.2

Numerous organic biocides have been used as additives into tin-free paints, however, the direct incorporation of small molecules into coating systems presents a number of issues. First, the release of the organic antifoulants must be sustained for several years in order to minimize the requirement for repainting of the vessel prior to scheduled drydocking. In addition, many currently employed organic antifoulants are toxic to marine foulers, which, with increased use could have an unfavorable impact on the marine ecosystem in the event of accumulation. The physical properties of the organic antifoulants can also have a profound impact on the integrity of a commercially available coating system, which in the absence of metal-based binders may require reformulation of coating systems.

Crucially, the mechanism by which the small molecule is incorporated into the coating system should permit retention of the activity of the small molecule. It is to be expected that structural modifications of the small molecule to impact on activity so that incorporating any active molecule into a coating system would be challenging.

SUMMARY OF THE INVENTION

The present inventors have sought to address the problem of providing an environmentally benign biocide that is suitable for incorporation into coating systems, and coating systems including such biocides.

At its most general, the present invention proposes that certain aryl-containing α,α-disubstituted amides should be provided with one or more selected substituents on the aryl, which substituents are suitable for attachment to a component, e.g. a polymer, of a coating composition. Surprisingly, amide compounds modified in this particular way retain useful activity.

In particular, derivatives of the small molecule antifouling additives described in PCT/SG2009/000175 are disclosed herein, which derivatives possess functionality that enables covalent attachment to, for example, self-polishing coating systems. The ability to covalently link additives to an existing coating system has potential to facilitate their controlled release, thus extending coating lifetime and enhancing antifouling properties. Further work has identified structural modifications that permit a stable bond to coating systems without significantly compromising biological potency, thereby enabling the release of bioactive molecules via pre-existing release chemistry.

In particular, the present application describes the synthesis and biological testing of a range of α-aryl amides bearing functionality to serve as a point of attachment to a marine coating system. A number of molecules are described which retain desirable antifouling properties (high potency against barnacle cyprid settlement yet low toxicity), while including ester or ether linkages that will enable covalent attachment to existing coating systems.

Compounds

The present invention pertains generally to a class of compounds referred to herein as "antifouling amide compounds", which compounds have the following general α,α-disubstituted structure:

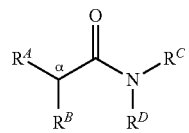

wherein one or both of $R^A$ and $R^B$ is an aryl and wherein $R^C$ and $R^D$ independently represent optionally substituted alkyl or together form a ring.

The present invention proposes that the aryl group of one or both of $R^A$ and $R^B$ of such compounds should be functionalised with one or more groups tailored to permit connection to coating systems (e.g. a polymer). Furthermore, the present invention proposes that such compounds having an aryl substituent that is a product of the cleavage of such a group from a coating system (e.g. a polymer) can retain useful activity.

The present invention pertains to such antifouling amide compounds, which exhibit biocidal or biostatic properties. Therefore, the antifouling amide compounds may also be referred to as "biocidal compounds" or "biostatic compounds".

Embodiments of the invention have the potential to enhance antifouling properties of existing marine coating systems. In particular, embodiments preferably have one or more of the following advantages: highly potent against barnacle settlement, low toxicity and are likely to degrade rapidly in the marine environment (environmentally benign).

Substitution of the aryl group with different functional groups can be employed as a point of attachment to tailor properties for different coatings and for different applications.

An advantage of this system lies in the potential to incorporate these molecules into an existing coating system and the release of the antifoulant will be directly linked to the lifetime of the coating.

In a first aspect the present invention provides a compound of formula (I) or a salt thereof:

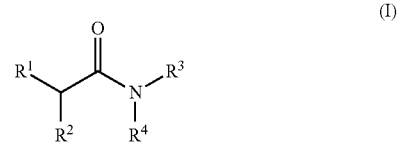

wherein
each of $R^1$ and $R^2$ is independently selected from
(A) aryl substituted with at least one of OH, $R^{S1}$OH, $OR^{S2}$, $R^{S1}OR^{S2}$, $OC(O)H$, $OC(O)R^{S2}$, $R^{S1}OC(O)H$, $R^{S1}OC(O)R^{S2}$, $C(O)OH$, $C(O)OR^{S2}$, $R^{S1}C(O)OH$, $R^{S1}C(O)OR^{S2}$, $OR^{S1}OH$, $OR^{S1}OR^{S2}$, $OR^{S1}OC(O)H$, $OR^{S1}OC(O)R^{S2}$, $OR^{S1}C(O)OH$ and $OR^{S1}C(O)OR^{S2}$,
wherein, if present, each $R^{S1}$ is independently optionally substituted $C_1$ to $C_5$ alkylene, and
wherein, if present, each $R^{S2}$ is independently selected from optionally substituted $C_1$ to $C_5$ alkyl, $C_2$ to $C_5$ alkenyl and $C_1$ to $C_5$ silyl-$C_1$ to $C_5$ alkylene.
and
(B) optionally substituted $C_3$ to $C_{12}$ alkyl
with the proviso that at least one of R' and $R^2$ is (A);
and
each of $R^3$ and $R^4$ are independently optionally substituted $C_1$ to $C_6$ alkyl, or $R^3$ and $R^4$ together form an optionally substituted 5 to 12-membered heterocycle which incorporates the nitrogen to which they are attached.

Whilst it is possible for both $R^1$ and $R^2$ to be (A), i.e. aryl, it is preferred that one of $R^1$ and $R^2$ is (B), i.e. $C_3$ to $C_{12}$ alkyl.

As described herein, $C_3$ to $C_{12}$ alkyl includes saturated and unsaturated, branched and unbranched $C_3$ to $C_{12}$ alkyl. In some preferred embodiments, the alkyl is unsaturated alkyl. In particular, preferably at least one of $R^1$ and $R^2$ is unsaturated $C_3$ to $C_{12}$ alkyl, preferably unsaturated $C_3$ to $C_{10}$ alkyl, preferably unsaturated $C_3$ to $C_8$ alkyl and most preferably unsaturated $C_3$ to $C_6$ alkyl. Thus, preferably at least one of $R^1$ and $R^2$ is $C_3$ to $C_{12}$ alkenyl, more preferably $C_3$ to $C_{10}$ alkenyl, more preferably $C_3$ to $C_8$ alkenyl and most preferably $C_3$ to $C_6$ alkenyl. Indeed, the addition of unsaturation can provide activity comparable to the saturated alkyl.

In such embodiments, preferably there is one carbon-carbon double bond in the alkenyl, for example one carbon-carbon double bond in $C_3$ to $C_{10}$ alkenyl, or one carbon-carbon double bond in $C_3$ to $C_6$ alkenyl. Suitably the carbon-carbon double bond is at the end of the alkenyl group, i.e. a terminal carbon-carbon double bond between the $O_n$ and $C_{n-1}$ carbons. $C_6$ alkenyls are particularly preferred. A particularly preferred alkenyl is $C_6$ alkenyl, most preferably 5-hexenyl (—$CH_2$—$(CH_2)_3$—$CH$=$CH_2$).

In embodiments, at least one of $R^1$ and $R^2$ is $C_3$ to $C_5$ alkyl. Alkyl groups, especially saturated alkyls, on the alpha carbon having between 3 and 5 carbon atoms in combination with one or more of the specified substituents on the aryl are particularly useful in providing antifouling activity whilst also exhibiting desirable solubility in sea water and degradability.

In embodiments at least one of $R^1$ and $R^2$ is $C_4$ alkyl, more preferably n-butyl. A $C_4$ alkyl group, and in particular n-butyl, on the alpha carbon, in combination with one or more of the specified substituents on the aryl, can provide surprisingly high levels of antifouling activity and is degraded at an appropriate rate.

It is preferred that $R^1$ is $C_3$ to $C_8$ alkyl, preferably $C_3$ to $C_6$ alkyl, more preferably $C_4$ to $C_6$ alkyl and most preferably $C_4$ alkyl or $C_6$ alkyl. Suitably $R^2$ is (A).

As described herein, one of $R^1$ and $R^2$ is (A), i.e. aryl (preferably $C_5$ to $C_{15}$ aryl, more preferably phenyl, as discussed below) and the other is $C_3$ to $C_{12}$ alkyl (preferably $C_3$ to $C_6$ alkyl, more preferably n-butyl or 5-hexenyl). The tests conducted by the present inventors demonstrate that desirable levels of antifouling activity are possible with this substitution pattern in conjunction with one or more of the specified substituents on the aryl.

Thus, it is preferred that one of $R^1$ and $R^2$ is selected from saturated $C_3$ to $C_5$ alkyl and $C_3$ to $C_{10}$ alkenyl. The alkyl (saturated or unsaturated) is optionally substituted, however, it is preferred that it is unsubstituted.

Suitably the aryl of (A) is $C_5$ to $C_{15}$ aryl, preferably $C_6$ to $C_{12}$ aryl, more preferably $C_6$ to $C_{10}$ aryl, and most preferably $C_6$ aryl. The aryl can be carboaryl or heteroaryl, but carboaryl is preferred. Especially preferred is phenyl.

Preferably $R^1$ is (B) and $R^2$ is

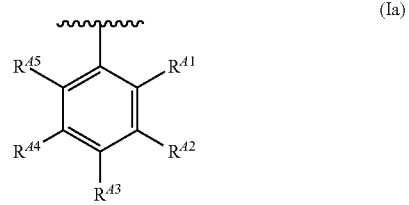

(Ia)

wherein each of $R^{41}$, $R^{42}$, $R^{43}$, $R^{44}$ and $R^{45}$ is independently selected from OH, $R^{S1}$OH, $OR^{S2}$, $R^{S1}OR^{S2}$, OC(O)H, OC(O)$R^{S2}$, $R^{S1}$OC(O)H, $R^{S1}$OC(O)$R^{S2}$, C(O)OH, C(O)$OR^{S2}$, $R^{S1}$C(O)OH, $R^{S1}$C(O)$OR^{S2}$, $OR^{S1}$OH, $OR^{S1}OR^{S2}$, $OR^{S1}$OC(O)H, $OR^{S1}$OC(O)$R^{S2}$, $OR^{S1}$C(O)OH, $OR^{S1}$C(O)$OR^{S2}$, H and $R^{S2}$,
wherein, if present, each $R^{S1}$ is independently optionally substituted $C_1$ to $C_5$ alkylene, and
wherein, if present, each $R^{S2}$ is independently selected from optionally substituted $C_1$ to $C_5$ alkyl, $C_2$ to $C_5$ alkenyl and $C_1$ to $C_5$ alkylsilyl-$C_1$ to $C_5$ alkylene,
with the proviso that at least one of $R^{41}$, $R^{42}$, $R^{43}$, $R^{44}$ and $R^{45}$ is not H or $R^{S2}$.

Suitably each $R^{S2}$ is independently optionally substituted $C_1$ to $C_3$ alkylene, preferably optionally substituted $C_1$ to $C_2$ alkylene and most preferably methylene. Suitably $R^{S1}$ is unsubstituted.

Suitably each $R^{S2}$ is independently selected from optionally substituted $C_1$ to $C_3$ alkyl, $C_2$ to $C_3$ alkenyl and $C_1$ to $C_3$ silyl-$C_1$ to $C_3$ alkylene. For the avoidance of doubt, silyl-alkylene referred to herein is an alkylene (e.g. —$CH_2$—$CH_2$—) substituted with a silyl such as $Si(Me)_3$.

Preferably each $R^{S2}$ is independently selected from optionally substituted $C_1$ to $C_2$ alkyl, $C_2$ to $C_3$ alkenyl and $C_1$ alkylsilyl-$C_1$ to $C_3$ alkylene. Especially preferred is that each $R^{S2}$ is independently selected from methyl, $CH_2$=CH— and $(Me)_3Si$—$CH_2$—$CH_2$—.

In particularly preferred embodiments each of $R^{41}$, $R^{42}$, $R^{43}$, $R^{44}$ and $R^{45}$ is independently selected from OH, OMe, C(O)OH, $CH_2$OH, $CH_2$OAc, OC(O)$CH_3$, $OCH_2$C(O)OH, $OCH_2$C(O)$OCH_3$, $OCH_2CH_2$OH, $OCH_2CH_2$OC(O)$CH_3$, $OCH_2CH_2Si(Me)_3$, OC(O)CH=$CH_2$ and H, with the proviso that at least one of $R^{41}$, $R^{42}$, $R^{43}$, $R^{44}$ and $R^{45}$ is not H.

In especially preferred embodiments each of $R^{41}$, $R^{42}$, $R^{43}$, $R^{44}$ and $R^{45}$ is independently selected from OH, OMe, $CH_2$OH, OC(O)$CH_3$, $OCH_2CH_2$OH, $OCH_2CH_2Si(Me)_3$, OC(O)CH=$CH_2$ and H, with the proviso that at least one of $R^{41}$, $R^{42}$, $R^{43}$, $R^{44}$ and $R^{45}$ is not H.

In even more preferred embodiments each of $R^{41}$, $R^{42}$, $R^{43}$, $R^{44}$ and $R^{45}$ is independently selected from OH, OMe, OC(O)CH=$CH_2$ and H, with the proviso that at least one of $R^{41}$, $R^{42}$, $R^{43}$, $R^{44}$ and $R^{45}$ is not H.

Whilst multiple substituents on the aryl are possible, it is preferred that at least two of $R^{41}$, $R^{42}$, $R^{43}$, $R^{44}$ and $R^{45}$ are H, more preferably that at least three of $R^{41}$, $R^{42}$, $R^{43}$, $R^{44}$ and $R^{45}$ are H. Thus, mono and di-substituted aryls (e.g. phenyl) are preferred.

The substituents can be at any of the 1- to 5-positions, i.e. ortho, meta or para substituents. However, the 3-position (meta) is preferred. Thus, suitably $R^{43}$ is not H.

Suitably $R^3$ and $R^4$ together form an optionally substituted 5 to 10-membered heterocycle, preferably a 5 to 7-membered heterocycle and most preferably a 6-membered heterocycle. It is especially preferred that the heterocycle is piperidine.

In particularly preferred embodiments $R^3$ and $R^4$ together form an optionally substituted 6-membered heterocycle which incorporates the nitrogen to which they are attached according to formula (II):

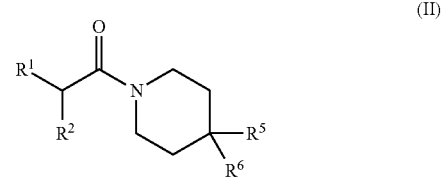

(II)

wherein each of $R^5$ and $R^6$ are independently selected from hydroxyl, optionally substituted $C_1$ to $C_6$ alkyl, optionally substituted phenyl and H. It is preferred that each of $R^5$ and $R^6$ are independently selected from hydroxyl, optionally substituted $C_1$ to $C_6$ alkyl and H. It is particularly preferred that $R^5$ and $R^6$ are H.

In other embodiments, each of $R^3$ and $R^4$ is independently selected from optionally substituted $C_1$ to $C_6$ alkyl, more preferably $C_1$ to $C_3$ alkyl.

Suitably $R^3$ and $R^4$ are unsubstituted. It is also preferred that each of $R^3$ and $R^4$ is saturated alkyl.

$R^3$ and $R^4$ can be the same or different. It is preferred that they are the same.

In embodiments, $R^3$ and $R^4$ are both methyl.

Suitably the compound is a compound of formula (III) or formula (IV)

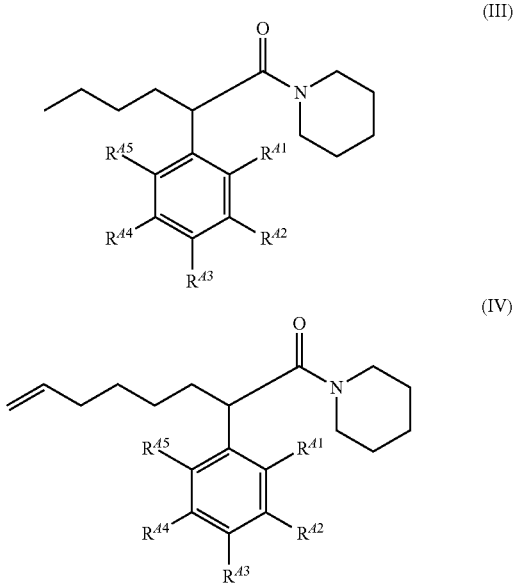

(III)

(IV)

wherein each of $R^{A1}$, $R^{A2}$, $R^{A3}$, $R^{A4}$ and $R^{A5}$ is independently selected from OH, $R^{S1}$OH, $OR^{S2}$, $R^{S1}OR^{S2}$, OC(O)H, OC(O)$R^{S2}$, $R^{S1}$OC(O)H, $R^{S1}$OC(O)$R^{S2}$, C(O)OH, C(O)O$R^{S2}$, $R^{S1}$C(O)OH, $R^{S1}$C(O)O$R^{S2}$, O$R^{S1}$OH, O$R^{S1}$O$R^{S2}$, O$R^{S1}$OC(O)H, O$R^{S1}$OC(O)$R^{S2}$, O$R^{S1}$C(O)OH, O$R^{S1}$C(O)O$R^{S2}$, H and $R^{S2}$, wherein, if present, each $R^{S1}$ is independently optionally substituted $C_1$ to $C_5$ alkylene, and wherein, if present, each $R^{S2}$ is independently selected from optionally substituted $C_1$ to $C_5$ alkyl, $C_2$ to $C_5$ alkenyl and $C_1$ to $C_5$ alkylsilyl-$C_1$ to $C_5$ alkylene, with the proviso that at least one of $R^{A1}$, $R^{A2}$, $R^{A3}$, $R^{A4}$ and $R^{A5}$ is not H or $R^{S2}$.

In embodiments, if present, each $R^{S1}$ is independently optionally substituted $C_1$ to $C_3$ alkylene, and wherein, if present, each $R^{S2}$ is independently selected from optionally substituted $C_1$ to $C_3$ alkyl and $C_2$ to $C_3$ alkenyl and $C_1$ to $C_3$ alkylsilyl-$C_1$ to $C_3$ alkylene.

Suitably the compound is selected from compounds 15.1, 15.2, 15.3, 15.4, 15.5, 15.6, 15.7, 16.1, 16.2, 16.3, 16.4, 16.5, 16.6, 16.7, 16.8, 16.9, 16.10, 16.11, 17.1, 17.2, 17.3, 17.4, 17.5, 17.6, 17.7, 17.8 and 17.9.

Preferably the compound is selected from compounds 15.3, 15.4, 15.5, 16.11, 17.1, 17.3, 17.4, 17.6, 17.8, 15.1, 16.1, 16.2, 16.4, 16.5, 16.6, 16.10 and 17.5. More preferably the compound is selected from compounds 15.3, 15.4, 15.5, 16.11, 17.1, 17.3, 17.4, 17.6 and 17.8.

In preferred embodiments these compounds (and polymers described herein) are incorporated into coatings in such a way that they are protected from premature degradation but released at a predetermined target time, after which they are degraded by bacteria in the environment. The skilled reader will be aware that the state of the art in polymer/coating chemistry provides several ways to deliver molecules in this way, depending on the requirements of the application.

In preferred embodiments, these compounds (and polymers described herein) are incorporated into conventional antifouling coatings as antifouling agents for the prevention of marine growth. For example, the compounds can be blended into existing acrylate paints and are therefore practical alternatives to the current coating options. In particular, these compounds may be offered as environmentally safer alternatives to reduce use of existing booster biocides in existing coating formulations, as a replacement for poorly-degradable existing booster biocides, and/or augment existing coating formulations to improve performance. In this connection, a number of the compounds are oils and suitably compatible for incorporation into coatings, for example silicon-based foul-release coatings. In embodiments, this compatibility may impart the coatings with increased effectiveness such that the coated substrate benefits from additional protection.

Furthermore, these compounds (and polymers described herein) may be applied in such way to reduce or replace copper/metal present in conventional antifouling coatings, thereby reducing the environmental impact of antifouling coatings.

Suitably, the compounds (and polymers described herein) may be used in the removal of marine organisms in seawater treatment processes such as in ballast water treatment and for control of marine growth in cooling water and desalination processes. The compounds (and polymers described herein) are particularly suited to processes where rapid degradation/removal of the active agent is necessary to prevent environmental contamination and for compliance purposes.

Polymers

The present invention also pertains generally to a class of polymers referred to herein as "antifouling polymers", which polymers comprise an antifouling amide compound, for example as a pendant group.

In a further aspect, the present invention provides a polymer comprising at least one repeating unit formed from an antifouling compound according to the first aspect.

In embodiments, the compound is incorporated into the polymer via free radical polymerisation or polymerisation of silyl-containing groups. Thus, preferably the polymer is selected from a polymer formed from one or more monomers having an unsaturated carbon-carbon bond, for example a vinyl or (meth)acrylate monomer; and a silicone polymer.

Suitably the polymer is a (meth)acrylate polymer. Suitably the polymer comprises repeating units derived from one or more of methylmethacrylate (MMA), hydroxyethyl acrylate (HEA) and vinyl pyrrolidinone (VP). Preferably the polymer is a copolymer.

In embodiments, the polymer comprises a pendant group according to formula X

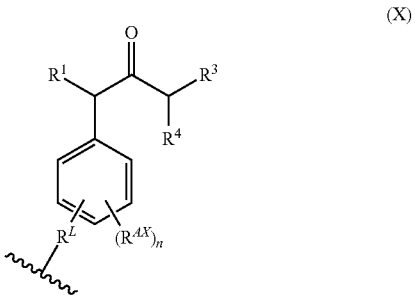

(X)

wherein $R^1$ is optionally substituted $C_3$ to $C_{12}$ alkyl each of $R^3$ and $R^4$ are independently optionally substituted $C_1$ to $C_6$ alkyl, or $R^3$ and $R^4$ together form an optionally substituted 5 to 12-membered heterocycle which incorporates the nitrogen to which they are attached, each $R^{AX}$ is independently selected from the options for any one of $R^{41}$ to $R^{45}$ described herein, n is an integer in the range 0 to 4, and wherein $R^L$ is a linker group.

The optional and preferred features in respect of $R^1$, $R^3$ and $R^4$ are as described above for the first aspect.

Preferably $R^L$ is a 1 to 5 atom chain, preferably a 1 to 3 atom chain, more preferably a 2 atom chain. Suitably the atoms of the chain are selected from C and O. Preferably the linker group comprises one or more of —O—, —C(O)— and —CH$_2$— units. Particularly preferred is a linker group having the structure: $\{[-O-]_a[-C(O)]_b[-CH_2-]_c\}_d$, wherein each of a, b, c and d are independently selected from an integer in the range 0 to 4, more preferably 0 to 2.

In embodiments, $R^L$ is selected from —O—, $R^{L1}$O, $OR^{L2}$, $R^{L1}OR^{L2}$, OC(O), $OC(O)R^{L2}$, $R^{L1}OC(O)$, $R^{L1}OC(O)R^{L2}$, C(O)O, $C(O)OR^{L2}$, $R^{L1}C(O)O$, $R^{L1}C(O)OR^{L2}$, $OR^{L1}O$, $OR^{L1}OR^{L2}$, $OR^{L1}OC(O)$, $OR^{L1}OC(O)R^{L2}$, $OR^{L1}C(O)O$ and $OR^{L1}C(O)OR^{L2}$ wherein, if present, each $R^{L1}$ is independently optionally substituted $C_1$ to $C_5$ alkylene, and wherein, if present, each $R^{L2}$ is independently optionally substituted $C_1$ to $C_5$ alkylene.

Thus, linker group $R^L$ can correspond to, e.g. be a radical formed from, the substituent $R^{41}$, $R^{42}$, etc of the corresponding "free" compound.

Preferably $R^L$ is —OC(O)—.

Suitably n is 0 or 1, preferably n is 0 (i.e. the aryl has no further substituents).

Suitably the pendant group is releasable from the polymer in the marine environment. In particular, it is preferred that the pendant group is releasable from the polymer by hydrolysis. For example, this permits the pendant (bioactive) group to be released in an aqueous environment.

In a further aspect, the present invention provides a polymer according to formula (XI):

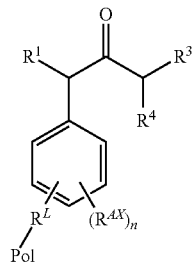

(XI)

wherein Pol is the polymer backbone, and wherein each of $R^1$, $R^3$, $R^4$, $R^{AX}$, n and $R^L$ is as defined in respect of formula (X).

Preferably the Tg of the polymer is higher than room temperature.

Preferably the molecular weight of the polymer, as measured by GPC, is at least 5 KDa, preferably at least 10 KDa.

Suitably the polymer is a slow release or sustained release polymer whereby an antifouling compound, preferably an antifouling compound of the first aspect, is released from the polymer in use.

In a further aspect, the present invention provides use of a compound of formula (I) or a salt thereof in a method of making a polymer.

In a further aspect, the present invention provides a polymer made by copolymerising a compound of formula (I) or a salt thereof with a comonomer. Preferably the comonomer is selected from a (meth)acrylate and vinyl monomer.

In a further aspect, the present invention provides use of a compound, polymer or coating composition as described herein in a method of reducing or preventing fouling.

Suitably the method of reducing or preventing fouling is a method of reducing or preventing biofilm formation by one or more of bacteria, fungi, algae and protozoans.

In a further aspect, the present invention provides a method of preventing or reducing fouling of a substrate, wherein the method comprises the step of applying a compound, polymer or coating as described herein to the substrate.

Suitably the antifouling amide compound or polymer is applied at in an amount and at a concentration effective to prevent or reduce fouling. Preferably the antifouling amide compound or polymer is provided at a standard concentration.

In a further aspect, the present invention provides a coating composition comprising a compound or a polymer as described herein.

In a further aspect, the present invention provides an antifouling composition comprising an antifouling amide compound or polymer as described herein.

In a further aspect, the present invention provides a coating composition comprising an antifouling amide compound or a polymer as described herein. Suitably the coating composition comprises conventional additives, for example a binder. Suitably the coating composition is a paint composition. For example, the composition can include an acrylate resin. Suitably the coating composition is a self-polishing paint, preferably an acrylic self polishing paint, or a silicone coating.

In a further aspect, the present invention provides a coating comprising an antifouling amide compound as described herein.

In a further aspect, the present invention provides a substrate having a coating applied thereto, wherein the coating comprises an antifouling amide compound or polymer as described herein. For example, the substrate may be a vessel, for example a boat.

In a further aspect, the present invention provides a bacteriostatic composition comprising an antifouling amide compound or polymer as described herein.

In a further aspect, the present invention provides a bacteriocidal composition comprising an antifouling amide compound or polymer as described herein.

In a further aspect, the present invention provides a biocidal composition comprising an antifouling amide compound or polymer as described herein.

In a further aspect, the present invention provides a biostatic composition comprising an antifouling amide compound or polymer as described herein.

In a further aspect, the present invention provides an antifoulant composition comprising an antifouling amide compound or polymer as described herein.

Any one or more of the optional and preferred features of any of the aspects may apply, singly or in combination, to any one of the other aspects.

BRIEF DESCRIPTION OF THE DRAWINGS

FIG. 1 shows average percentage settlement of barnacles in wells coated with polymers containing repeating units derived from a compound (16.11) of the present invention.

Settlement on the control coating was similar to that for uncoated polystyrene. Whereas when increased amounts of P(MMA-co-16.11-co-VP) resulted in decline in barnacle settlement, with no settlement for test treatments >40 µl.

DETAILED DESCRIPTION OF THE INVENTION

Chemical Terms

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond. Compounds and/or groups may be partially unsaturated or fully unsaturated.

The term "carbo," "carbyl," "hydrocarbo," and "hydrocarbyl," as used herein, pertain to compounds and/or groups which have only carbon and hydrogen atoms.

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The phrase "optionally substituted," as used herein, pertains to a parent group which may be unsubstituted or which may be substituted.

Unless otherwise specified, the term "substituted," as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g., $C_1$ to $C_4$, $C_1$ to $C_6$, etc.) denote the number of carbon atoms, or range of number of carbon atoms. For example, the term "$C_1$ to $C_4$alkyl," as used herein, pertains to an alkyl group having from 1 to 4 carbon atoms. Examples of groups of alkyl groups include $C_1$ to $C_4$alkyl ("lower alkyl"), and $C_2$ to $C_6$ alkyl. Note that the first prefix may vary according to other limitations; for example, for unsaturated alkyl groups, the first prefix must be at least 2; for cyclic and branched alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$) and hexyl ($C_6$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$) and n-hexyl ($C_6$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

Hydroxy-$C_1$-$C_6$ alkyl: The term "hydroxy-$C_1$-$C_6$ alkyl," as used herein, pertains to a $C_1$-$C_6$ alkyl group in which at least one hydrogen atom (e.g., 1, 2, 3) has been replaced with a hydroxy group. Examples of such groups include, but are not limited to, —CH$_2$OH, —CH$_2$CH$_2$OH, and —CH(OH)CH$_2$OH.

Hydrogen: —H. Note that if the substituent at a particular position is hydrogen, it may be convenient to refer to the compound or group as being "unsubstituted" at that position.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{5-20}$aryl, $C_{5-15}$aryl, $C_{5-12}$aryl, $C_{5-10}$aryl, $C_{5-7}$aryl, $C_{5-6}$aryl, $C_5$aryl, and $C_6$aryl.

The ring atoms may be all carbon atoms, as in "carboaryl groups." Examples of carboaryl groups include $C_{3-20}$carboaryl, $C_{5-20}$carboaryl, $C_{5-15}$carboaryl, $C_{5-12}$carboaryl, $C_{5-10}$carboaryl, $C_{5-7}$carboaryl, $C_{5-6}$carboaryl, $C_5$carboaryl, and $C_6$carboaryl.

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups." Examples of heteroaryl groups include $C_{3-20}$heteroaryl, $C_{5-20}$heteroaryl, $C_{5-15}$heteroaryl, $C_{5-12}$neteroaryl, $C_{5-10}$heteroaryl, $C_{5-7}$heteroaryl, $C_{5-6}$heteroaryl, $C_5$heteroaryl, and $C_6$heteroaryl.

Halo (or halogen): —F, —Cl, —Br, and —I.

Hydroxy: —OH.

Silyl: —SiR$_3$, where R is a silyl substituent, for example, —H, a $C_{1-7}$alkyl group, a $C_{3-20}$heterocyclylgroup, or a $C_{5-20}$aryl group, preferably —H, a $C_{1-7}$alkyl group, or a $C_{5-20}$aryl group. Examples of silyl groups include, but are not limited to, —SiH$_3$, —SiH$_2$(CH$_3$), —SiH(CH$_3$)$_2$, —Si(CH$_3$)$_3$, —Si(Et)$_3$, —Si(iPr)$_3$, —Si(tBu)(CH$_3$)$_2$, and —Si(tBu)$_3$.

Oxysilyl: —Si(OR)$_3$, where R is an oxysilyl substituent, for example, —H, a $C_{1-7}$alkyl group, a $C_{3-20}$heterocyclylgroup, or a $C_{5-20}$aryl group, preferably —H, a $C_{1-7}$alkyl group, or a $C_{5-20}$aryl group. Examples of oxysilyl groups include, but are not limited to, —Si(OH)$_3$, —Si(OMe)$_3$, —Si(OEt)$_3$, and —Si(OtBu)$_3$.

Siloxy (silyl ether): —OSiR$_3$, where SiR$_3$ is a silyl group, as discussed above. Oxysiloxy: —OSi(OR)$_3$, wherein OSi(OR)$_3$ is an oxysilyl group, as discussed above.

Silyl-alkylene: -alkylene-SiR$_3$, where R is a silyl substituent as discussed above. For example, —CH$_2$—CH$_2$—Si(Me)$_3$.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, an environmentally-acceptable salt.

Examples of suitable salts are discussed in Berge et al., 1977, "Pharmaceutically Acceptable Salts," J. Pharm. Sci., Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3$+, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

Unless otherwise specified, a reference to a particular compound also include solvated forms thereof.

Certain Preferred Substituents

In one preferred embodiment, the substituent(s), often referred to herein as R, are independently selected from: halo; hydroxy; ether (e.g., C$_{1-7}$alkoxy); formyl; acyl (e.g., C$_{1-7}$alkylacyl, C$_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., C$_{1-7}$alkylthio); sulfonic acid; sulfonate; sulfone; sulfonyloxy; sulfinyloxy; sulfamino; sulfonamino; sulfinamino; sulfamyl; sulfonamido; C$_{1-7}$alkyl (including, e.g., unsubstituted C$_{1-7}$hydroxyalkyl, C$_{1-7}$carboxyalkyl, C$_{1-7}$aminoalkyl, C$_{5-20}$aryl-C$_{1-7}$alkyl); C$_{3-20}$heterocyclyl; or C$_{5-20}$aryl (including, e.g., C$_{5-20}$carboaryl, C$_{5-20}$heteroaryl, C$_{1-7}$alkyl-C$_{5-20}$aryl and C$_{5-20}$haloaryl)).

In one preferred embodiment, the substituent(s), often referred to herein as R, are independently selected from:
—F, —Cl, —Br, and —I;
—OH;
—OMe, —OEt, —O(tBu), and —OCH$_2$Ph;
—SH;
—SMe, —SEt, —S(tBu), and —SCH$_2$Ph;
—C(=O)H;
—C(=O)Me, —C(=O)Et, —C(=O)(tBu), and —C(=O)Ph;
—C(=O)OH;
—C(=O)OMe, —C(=O)OEt, and —C(=O)O(tBu);
—C(=O)NH$_2$, —C(=O)NHMe, —C(=O)NMe$_2$, and —C(=O)NHEt;
—NHC(=O)Me, —NHC(=O)Et, —NHC(=O)Ph, succinimidyl, and maleimidyl;
—NH$_2$, —NHMe, —NHEt, —NH(iPr), —NH(nPr), —NMe$_2$, —NEt$_2$, —N(iPr)$_2$, —N(nPr)$_2$, $^-$N(nBu)$_2$, and —N(tBu)$_2$;
—CN;
—NO$_2$;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$;
—CH$_2$OH, —CH$_2$CH$_2$OH, and —CH(OH)CH$_2$OH;
—CH$_2$NH$_2$, —CH$_2$CH$_2$NH$_2$, and —CH$_2$CH$_2$NMe$_2$; and, optionally substituted phenyl.

In one preferred embodiment, the substituent(s), often referred to herein as R, are independently selected from:
—F, —Cl, —Br, —I, —OH, —OMe, —OEt, —SH, —SMe, —SEt, —C(=O)Me, —C(=O)OH, —C(=O)OMe, —CONH$_2$, —CONHMe, —NH$_2$, —NMe$_2$, —NEt$_2$, —N(nPr)$_2$, —N(iPr)$_2$, —CN, —NO$_2$, -Me, -Et, —CF$_3$, —OCF$_3$, —CH$_2$OH, —CH$_2$CH$_2$OH, —CH$_2$NH$_2$, —CH$_2$CH$_2$NH$_2$, and -Ph.

In one preferred embodiment, the substituent(s), often referred to herein as R, are independently selected from: hydroxy; ether (e.g., C$_{1-7}$alkoxy); ester; amido; amino; and, C$_{1-7}$alkyl (including, e.g., unsubstituted C$_{1-7}$haloalkyl, C$_{1-7}$hydroxyalkyl, C$_{1-7}$carboxyalkyl, C$_{1-7}$aminoalkyl, C$_{5-20}$aryl-C$_{1-7}$alkyl).

In one preferred embodiment, the substituent(s), often referred to herein as R, are independently selected from:
—OH;
—OMe, —OEt, —O(tBu), and —OCH$_2$Ph;
—C(=O)OMe, —C(=O)OEt, and —C(=O)O(tBu);
—C(=O)NH$_2$, —C(=O)NHMe, —C(=O)NMe$_2$, and —C(=O)NHEt;
—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—CH$_2$OH, —CH$_2$CH$_2$OH, and —CH(OH)CH$_2$OH; and,
—CH$_2$NH$_2$, —CH$_2$CH$_2$NH$_2$, and —CH$_2$CH$_2$NMe$_2$.

Other Terms

As used herein, the term "fouling" refers to the attachment and growth of microorganisms and small organisms to a substrate exposed to, or immersed in, a liquid medium, for example an aqueous medium, as well as to an increase in number of the microorganisms and/or small organisms in a container of the liquid medium.

Accordingly "foulers" or "microfoulers" are used interchangeably and refer to the organisms that foul a substrate. Fouling may occur in structures exposed to or immersed in fresh water as well as in sea water. In particular, the term may be used to refer to a solid medium or substrate exposed to, or immersed in sea water.

Accordingly, the term "antifouling" refers to the effect of preventing, reducing and/or eliminating fouling. Antifouling agents or compounds are also called "antifoulants".

An antifoulant compound is usually applied at a standard concentration which is the concentration that is effective for its purpose. Accordingly, a concentration less than or below the standard concentration is one where the antifoulant is not effective when it is used alone.

The term "substrate" as used herein refers to a solid medium such as surfaces of structures or vessels exposed to, or immersed in a liquid medium. The liquid medium may be fresh water or seawater and may be a body of water in a manmade container such as a bottle, pool or tank, or the liquid may be uncontained by any manmade container such as seawater in the open sea.

A "structure" as used herein refers to natural geological or manmade structures such as piers or oil rigs and the term "vessel" refers to manmade vehicles used in water such as boats and ships.

The "microorganisms" referred to herein include viruses, bacteria, fungi, algae and protozoans. "Small organisms" referred to herein can include organisms that commonly foul substrates exposed to, or immersed in, fresh water or seawater such as crustaceans, bryozoans and molluscs, particularly those that adhere to a substrate. Examples of such small organisms include barnacles and mussels and their larvae. Small organisms can also be called small animals. The term "organism" referred to herein is to be understood accordingly and includes microorganisms and small organisms.

The term "marine organism" as used herein refers to organisms whose natural habitat is sea water. The terms "marine microorganism" and "marine small organism" are to be understood accordingly.

Further, the term "microfouling" refers to fouling by microorganisms and the term "macrofouling" refers to fouling by organisms larger than microorganisms such as small organisms defined above.

The terms "biocide" or "biocidal compound" refer to compounds that inhibit the growth of microorganisms and small organisms by killing them. The terms "biostatic" or "biostatic compound" refer to compounds that inhibit the growth of microorganisms or small organisms by preventing them from reproducing and not necessarily by killing them.

The term "degradation" as used herein refers to the chemical breakdown or modification of a compound in water, preferably sea water.

The term "growth" as used herein refers to both the increase in number of microorganisms and small organisms, as well to the development of a small organism from juvenile to adult stages. Accordingly, biocides and biostatics can be applied as a treatment to a body of liquid or to a substrate surface to inhibit the growth of microorganisms and small organisms. As such, biocides and biostatics can be antifoulants and can prevent, reduce or eliminate biofilm formation.

Accordingly, the terms "bacteriocidal" and "bacteriostatic" refer to effects of compounds on bacteria.

The term "bioactivity" as used herein refers to the effect of a given agent or compound, such as a biocidal or biostatic compound, on a living organism, particularly on microorganisms or small organisms.

A "biofilm" is a complex aggregation of microorganisms, usually bacteria or fungi, marked by the excretion of a protective and adhesive matrix. Biofilms are also often characterized by surface attachment, structural heterogeneity, genetic diversity, complex community interactions, and an extracellular matrix of polymeric substances. Biofilms may also be more resistant to antibiotics compared to unaggregated bacteria due to the presence of the matrix.

The term "pharmaceutical" as it relates to a use, agent, compound or composition, refers to the medical treatment of a disease or disorder in humans or animals. Accordingly, a pharmaceutical compound is a compound used for the medical treatment of a disease or disorder in humans or animals.

As used herein, the term "standard concentration" as it pertains to an anti-fouling agent or compound, refers to the concentration at which the agent or compound is effective against microorganisms or small organisms at which it are directed when that agent or compound is used alone. Accordingly, the term "effective" means having a desired effect and the term "below standard concentration" refers to the level at which the agent or compound is not effective when used alone.

Examples Part 1—Compounds

Synthesis of Compounds

Several methods for the chemical synthesis of compounds of the present invention are described herein. These and/or other well known methods may be modified and/or adapted in known ways in order to facilitate the synthesis of additional compounds within the scope of the present invention.

The amides may be prepared according to the following general methodologies

Method A

The synthesis of alkoxylated substituted compounds such as the 15-series compounds is based on a two step protocol in which commercially available phenylacetic acid derivatives undergo DCC mediated amide formation with piperidine (Scheme 1). Subsequent alkylation of the resultant 2-arylacetamides then proceeds upon treatment with LDA and bromobutane under standard conditions.

Scheme 1

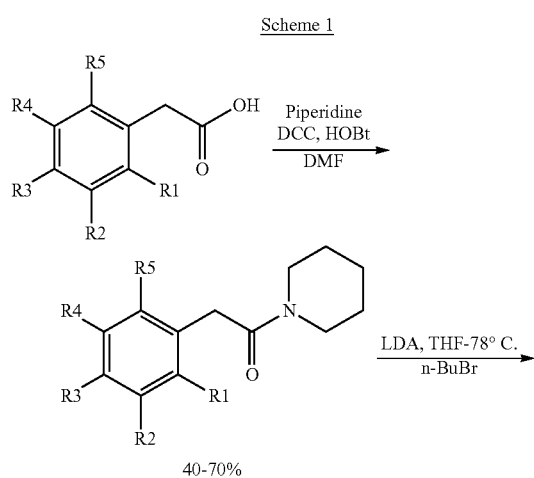

40-70%

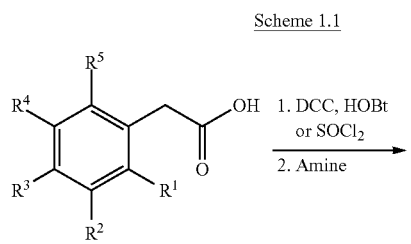

15-60%

The same methodology was also adopted for the dialkyl amides. Thus, the synthesis of the methoxy- and hydroxyaryl congeners of the unsubstituted parent compound is based on a three or four step protocol in which commercially available phenylacetic acid derivatives are first converted to either the piperdine or dimethyl amides via the corresponding acid chlorides or benzotriazolyl esters. Subsequent LDA promoted alkylation with either 1-bromobutane or 6-bromo-1-hexene affords the desired methoxyaryl compounds in low to good yields as shown in Scheme 1.1.

Scheme 1.1

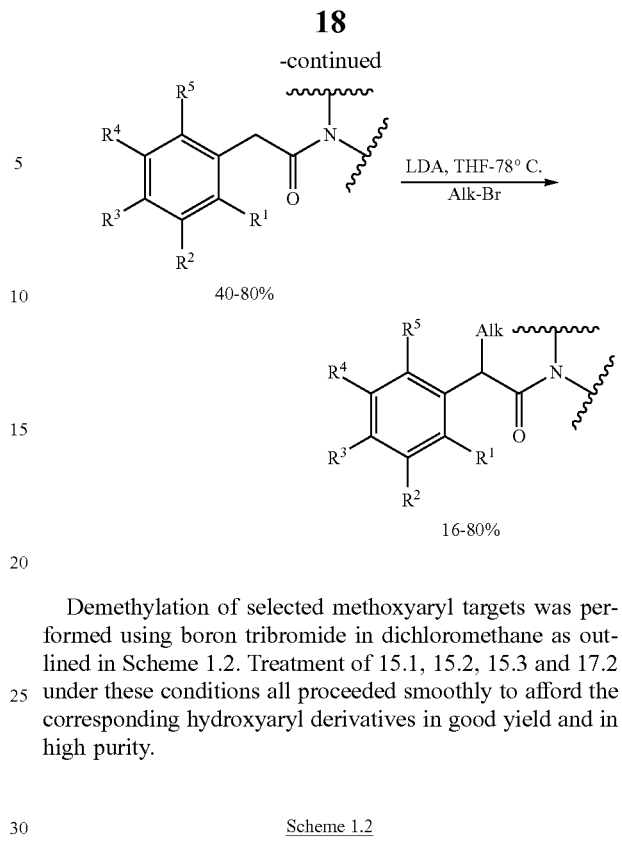

40-80%

16-80%

Demethylation of selected methoxyaryl targets was performed using boron tribromide in dichloromethane as outlined in Scheme 1.2. Treatment of 15.1, 15.2, 15.3 and 17.2 under these conditions all proceeded smoothly to afford the corresponding hydroxyaryl derivatives in good yield and in high purity.

Scheme 1.2

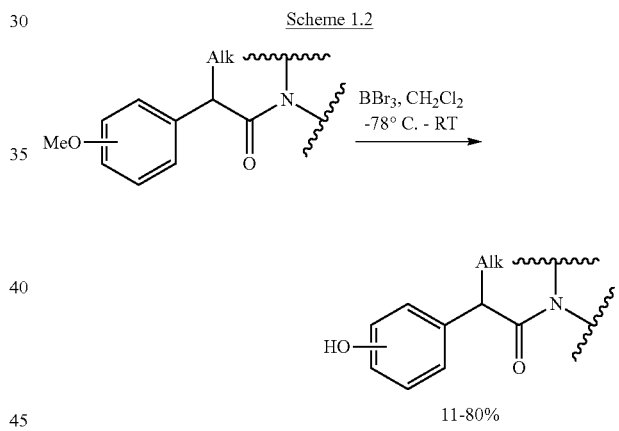

11-80%

Method B

The synthesis of hydroxymethylated compounds and acetylated analogues were accessed from the readily synthesized amides following standard protection and alkylation protocols (Scheme 2). Acetylation of the p-derivative afforded compounds in good isolated yield.

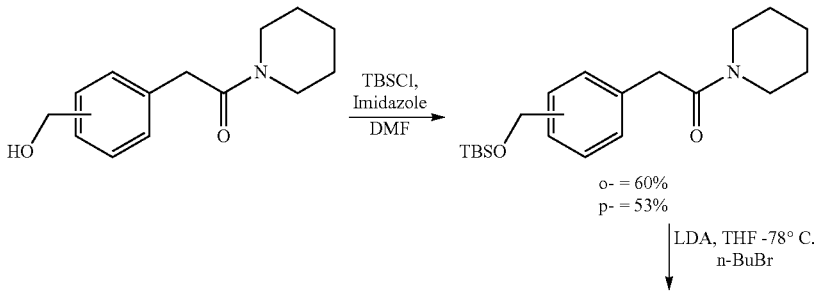

o- = 60%
p- = 53%

LDA, THF -78° C.
n-BuBr

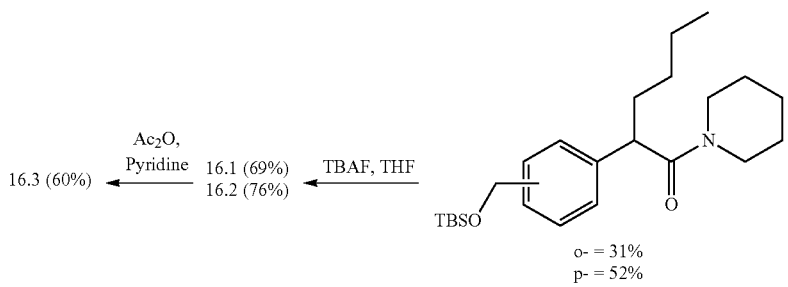

More specifically, in order to gain access the hydroxymethylated congeners of 12.1 and their acetate derivatives, it was necessary to use different synthetic routes based on the commercial availability of the phenylacetic acid derivatives. Whilst p-hydroxymethylphenylacetic acid is commercially available and was able to be used directly in a coupling reaction with piperidine, the corresponding o-hydroxymethylphenylacetic acid was not commercially available. Hence the requisite amide was accessed by nucleophilic ring opening of commercially available isochromanone with piperidine in moderate isolated yield (Scheme 2.1 below). With the o- and p-hydroxymethylamides in hand, treatment with tert-butyldimethylsilyl (TBS) chloride in the presence of imidazole afforded the corresponding TBS ethers in moderate yield and these underwent alkylation to furnish 16.1 and 16.2 in their protected form. Treatment of the TBS ethers with TBAF in THF resulted in removal of the TBS protecting group to afford 16.1 and 16.2 in near quantitative yields. Compound 16.3 was then isolated following treatment of 16.2 with acetic anhydride in pyridine. This is shown in Scheme 2.1 below, being a modified version of Scheme 2.

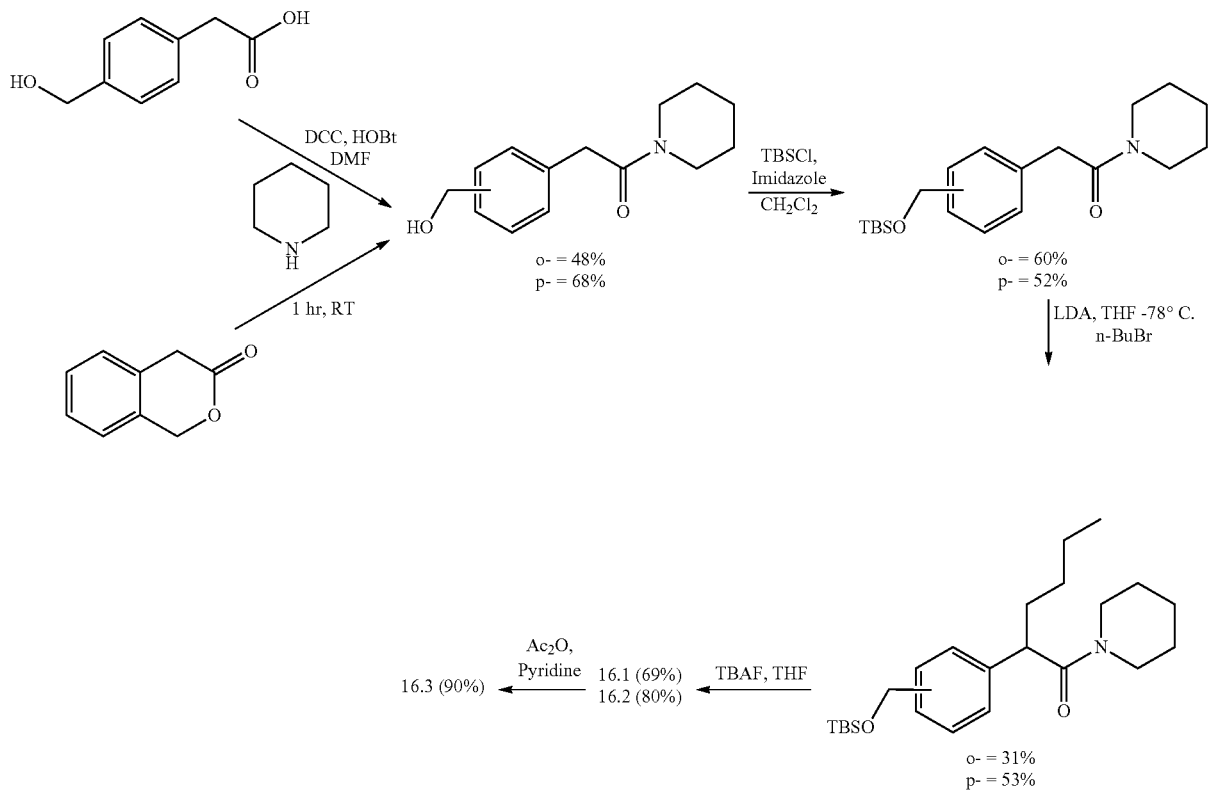

The procedure to convert 16.2 directly to 17.9 was a two step process whereby Swern oxidation to the corresponding aldehyde was performed prior to treatment with Oxone®. The desired acid was obtained in moderate overall yield (Scheme 3).

Scheme 3

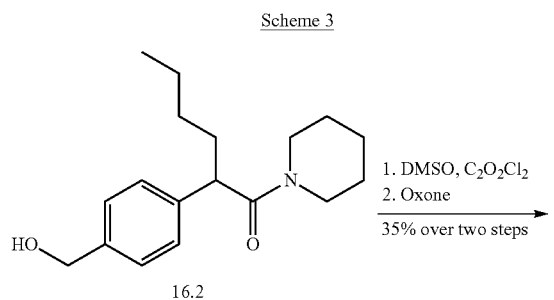

The remaining targeted congeners of 12.1 could all be accessed by modification of 16.5 by treatment with an appropriate electrophile. In all cases the target compounds were obtained in moderate to excellent yield. A summary of these reactions are shown in Scheme 4.

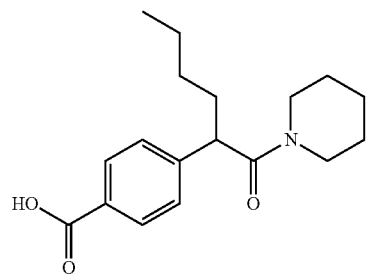

Scheme 4

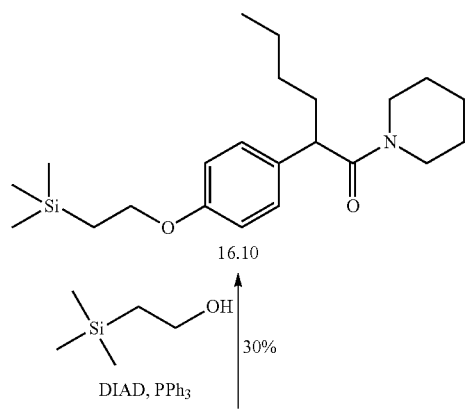

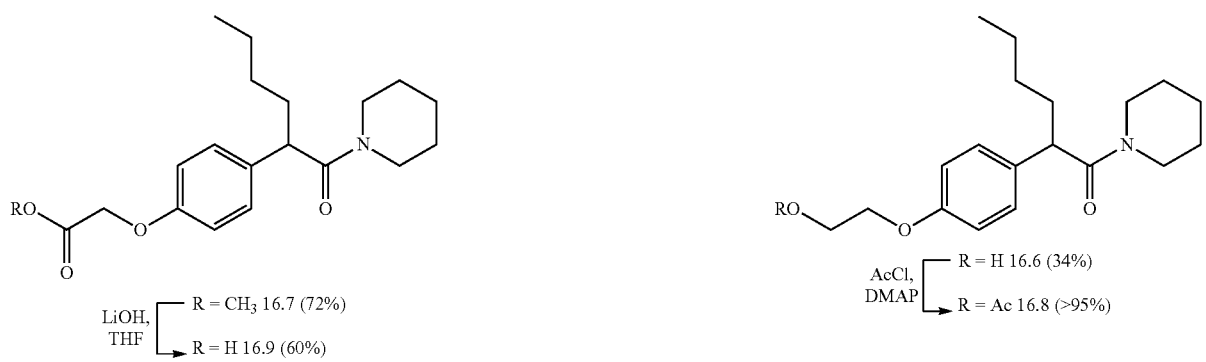

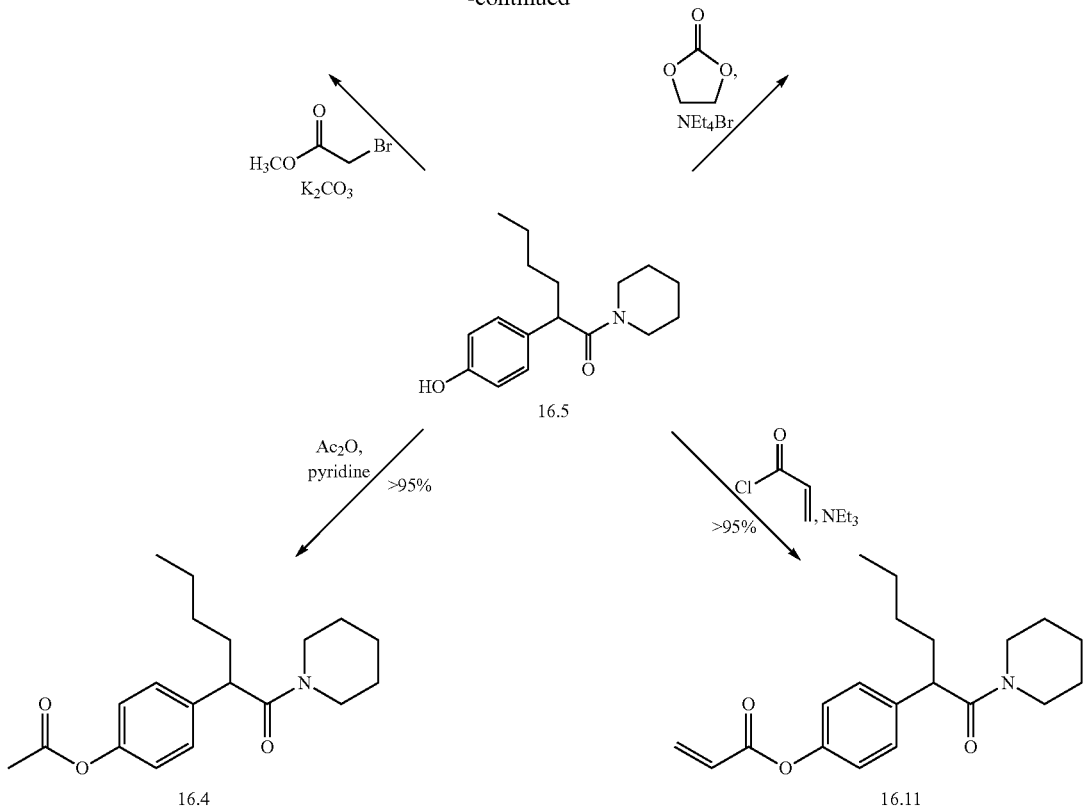

Using the above methodologies, the compounds based on the following structure were synthesised, and are preferred embodiments (reference compound excluded):

(III)

| $R^{A1}$ | $R^{A2}$ | $R^{A3}$ | $R^{A4}$ | $R^{A5}$ | Compound |
|---|---|---|---|---|---|
| H | H | H | H | H | 12.1 (reference) |
| H | H | OMe | H | H | 15.1 |
| H | OMe | H | H | H | 15.2 |
| OMe | H | H | H | H | 15.3 |
| H | OMe | H | OMe | H | 15.4 |
| H | OMe | H | H | OMe | 15.5 |
| H | OMe | OMe | H | H | 15.6 |
| OMe | H | OMe | H | H | 15.7 |
| CH$_2$OH | H | H | H | H | 16.1 |
| H | H | CH$_2$OH | H | H | 16.2 |
| H | H | CH$_2$OAc | H | H | 16.3 |
| H | H | OH | H | H | 16.5 |
| H | OH | H | H | H | 17.5 |
| OH | H | H | H | H | 17.4 |

Additionally, the following compounds were synthesised, and are preferred embodiments.

| $R^{A1}$ | $R^{A2}$ | $R^{A3}$ | $R^{A4}$ | $R^{A5}$ | Compound No. |
|---|---|---|---|---|---|
| H | H | HOC(O)— | H | H | 17.9 |
| CH$_2$OH | H | H | H | H | 16.1 |
| H | H | CH$_2$OH | H | H | 16.2 |
| H | H | CH$_2$OAc | H | H | 16.3 |
| H | H | CH$_3$C(O)O— | H | H | 16.4 |
| H | H | HOC(O)CH$_2$O— | H | H | 16.9 |
| H | H | CH$_3$OC(O)CH$_2$O— | H | H | 16.7 |
| H | H | HOCH$_2$CH$_2$O— | H | H | 16.6 |
| H | H | CH$_3$C(O)OCH$_2$CH$_2$O— | H | H | 16.8 |
| H | H | (CH$_3$)$_3$SiCH$_2$CH$_2$O— | H | H | 16.10 |
| H | H | CH$_2$CHC(O)O— | H | H | 16.11 |

Additionally, the compounds of the following structure were synthesised, and are preferred embodiments

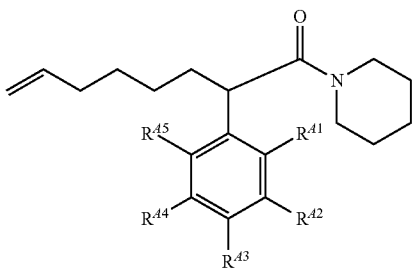

| $R^{A1}$ | $R^{A2}$ | $R^{A3}$ | $R^{A4}$ | $R^{A5}$ | Compound No. |
|---|---|---|---|---|---|
| H | H | OCH$_3$ | H | H | 17.1 |
| H | H | OH | H | H | 17.6 |

Additionally, the compounds of the following structure were synthesised, and are preferred embodiments

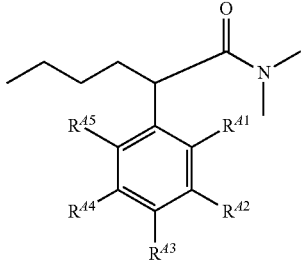

| $R^{A1}$ | $R^{A2}$ | $R^{A3}$ | $R^{A4}$ | $R^{A5}$ | Compound No. |
|---|---|---|---|---|---|
| H | H | OCH$_3$ | H | H | 17.2 |
| H | H | OH | H | H | 17.7 |

Additionally, the compounds of the following structure were synthesised, and are preferred embodiments

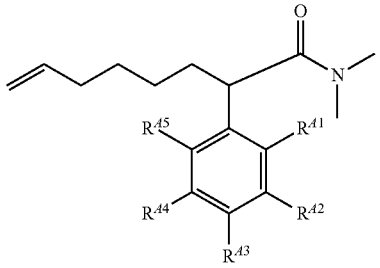

| $R^{A1}$ | $R^{A2}$ | $R^{A3}$ | $R^{A4}$ | $R^{A5}$ | Compound No. |
|---|---|---|---|---|---|
| H | H | OCH$_3$ | H | H | 17.3 |
| H | H | OH | H | H | 17.8 |

These compounds were tested for bioactivity against barnacles.

Synthesis Methods and Data for Selected Amide Derivatives

Characterisation

Proton ($^1$H) and carbon ($^{13}$C) NMR spectra were recorded on a Bruker NMR spectrometer operating at 400 MHz for $^1$H and 75.4 MHz for $^{13}$C. Deuterochloroform (CDCl$_3$) was used as the solvent unless otherwise indicated. Chemical shifts (d) are reported as the shift in parts per million (ppm) from tetramethylsilane (TMS, 0.00 ppm). NMR spectra recorded in CDCl$_3$ were referenced to the residual chloroform singlet (7.26 ppm) for $^1$H, and the central peak of the CDCl$_3$ triplet (77.00 ppm) for $^{13}$C. $^1$H NMR spectroscopic data are reported as follows: chemical shift (δ), multiplicity (s: singlet, d: doublet, t: triplet, q: quartet, qt: quintet, m: multiplet, dd: doublet of doublets, etc., br: broad), coupling constant (J Hz) and relative integral (number of protons). $^{13}$C spectroscopic data are reported as chemical shift (δ) and assignment where possible. Infrared spectra were recorded on a Bio-rad Excalibur Series TFS 3000MX FTIR. Samples were run as thin liquid films on NaCl plates. IR spectral data is reported as follows: frequency ($v_{max}$ cm$^{-1}$), strength (vs: very strong, s: strong, m: medium, w: weak). High resolution EI mass spectra were recorded on a Thermo Finnigan MAT XP95 mass spectrometer. Analytical thin layer chromatography (tlc) was conducted on aluminium sheets coated with silica gel F$_{254}$ (Merck). The chromatograms were analysed at a wavelength of 254 nm (where appropriate) and/or developed using an acidic solution (5% H$_2$SO$_4$) of potassium permanganate in water followed by heating. All solvents used were of AR grade and purified by literature procedures where appropriate (Armarego, 2003).

General Procedure—DCC Mediated Amide Bond Formation

To a cooled (0° C.) stirred solution of phenylacetic acid deriVative (1 equiv.) in DMF (1.2 mL/mmol) was added DCC (1.1 equiv.) and HOBt (1.1 equiv.). The resulting mixture was allowed to stir for 1 hour, by which time a heavy colourless precipitate was evident. Piperidine (1.1 equiv.) was added to the reaction mixture and stirring was continued for a further two hours, after which time the reaction mixture was filtered. The mother liquor was taken up in EtOAc and washed successively with saturated NaHCO$_3$ and water (×3, 2.4 mL/mmol). The organic layer was dried (MgSO$_4$) and concentrated in vacuo to afford the crude amides, which were purified by flash column chromatography using the solvent systems specified.

General Procedure—Amide Bond Formation Via Acid Chlorides

To a cooled (0° C.) stirred solution of methoxyphenylacetic acid in DCM (0.4 mL mmol$^{-1}$) was added thionyl chloride (0.4 mL mmol$^{-1}$). The resulting mixture was allowed to warm to room temperature and was heated at 50° C. for 2 hours after which time the reaction mixture was cooled to room temperature and carefully poured onto ice. The organic layer was dried (MgSO$_4$) and concentrated in vacuo to afford the desired acid chloride which was used without further purification.

For piperidine amides, the appropriate amount of acid chloride (1 mol. equiv.) was dissolved in an equal amount of dry CH$_2$Cl$_2$ and added slowly to a cooled (0° C.) solution of piperidine (2 mol. equiv.) in CH$_2$Cl$_2$ (1 mL mmol$^{-1}$). The resulting mixture was allowed to warm to room temperature and stirred for a further two hours. The crude reaction mixture was washed with water and the organic layer dried (MgSO$_4$) and concentrated in vacuo to afford the desired amide. No further purification was necessary.

For dimethyl amides, the appropriate amount of acid chloride was slowly added to cooled (0° C.) 40% solution of dimethylamine in water (10 mol. equiv.) and stirred for 2 hours after warming to room temperature. CH$_2$Cl$_2$ was added to the reaction mixture and the organic layer was washed with water, dried (MgSO$_4$) and concentrated in vacuo to afford the desired amide.

General Procedure—α-Alkylation

To a cooled (−78° C.) stirred solution of freshly distilled diisopropylamide (1 equiv.) in dry THF (2 mL/mmol) was added n-butyllithium in hexanes (1 equiv). The resulting reaction mixture became pale yellow and was stirred for 10-15 minutes at −78° C. prior to the careful addition of the desired amide (0.95 equiv.). The resulting mixture was stirred for 1 hour at which point bromobutane (1 equiv.) was'added. The resulting mixture was allowed to warm to room temperature over a number of hours (at least 3) and continued stirring for a further 13 hours (16 hours in total). The reaction was quenched by the careful dropwise addition of water to the reaction mixture. Following this, water was added to the reaction mixture and the aqueous phase removed. The organic layer was washed with water followed by brine, dried (MgSO$_4$) and concentrated under reduced pressure. Purification was carried out by flash column chromatography using the solvent systems specified.

Compound 15.1

2-(4-methoxy)phenyl-1-(piperidin-1-yl)ethanone

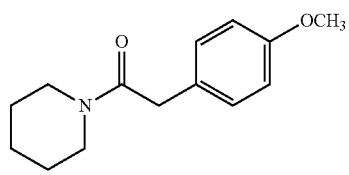 [SMILES: COc1ccc(CC(=O)N2CCCCC2)cc1]

The title compound was prepared from 4-methoxyphenylacetic acid (1.0 g, 6.1 mmol) following the general procedure for amide bond formation. The product was isolated as a colourless oil (1.0 g, 65%) following purification by flash column chromatography (EtOAc, Rf=0.5). $^1$H NMR (400 MHz, CDCl$_3$) δ1.35 (m, 2H); 1.49 (m, 2H); 1.57 (m, 2H); 3.35 (m, 2H); 3.55 (m, 2H); 3.64 (s, 2H); 3.77 (s, 3H); 6.85 (d, J=8.4 Hz, 2H); 7.16 (d, $^2$J=8.4 Hz 2H). $^{13}$C NMR (75 MHz, CDCl$_3$) δ24.47, 25.52, 26.25, 40.26, 42.90, 47.25, 55.28, 114.08, 127.47, 129.61, 158.27, 169.60. HRMS (ESI+ ion) m/z calcd for C$_{14}$H$_{20}$NO$_2$ 234.1489, found 234.1496.

2-(4-methoxy)phenyl-(1-piperidin-1-yl)hexanone

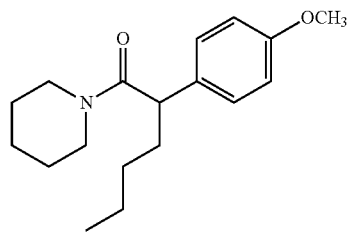

15.1

The title compound was prepared following the general procedure outline for n-alkylation from 2-(4-methyoxy)phenyl-1-(piperidin-1-ypethanone (740 mg, 3.41 mmol). The title compound was isolated as a pale yellow oil (160 mg, 16%) following purification by flash column chromatography (20% EtOAc in hexane, Rf=0.6). $^1$H NMR (400 MHz, CDCl$_3$) δ0.83 (t, J=7 Hz, 3H); 1.03 (m, 1H); 1.14 (m, 1H); 1.2-1.6 (multiple signals, 8H); 1.68 (m, 1H); 2.05 (m, 1H); 3.31-3.45 (2×m, 3H); 3.64 (m, 2H); 3.78 (s, 3H); 6.83 (d, J=8.9 Hz, 2H); 7.18 (d, J=8.9 Hz 2H). $^{13}$C NMR (75 MHz, CDCl$_3$) δ14.05, 22.74, 24.60, 25.60, 26.16, 30.07, 34.81, 43.15, 46.64, 47.78, 55.24, 113.98, 128.29, 133.03, 158.34, 171.67. HRMS (ESI+ 1 ion) m/z calcd for C$_{18}$H$_{29}$NO$_2$ 290.2115, found 290.2130.

Compound 15.7

2-(2,4-dimethoxy)phenyl-1-(piperidin-1-yl)ethanone

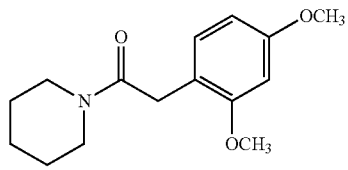 [SMILES: COc1ccc(CC(=O)N2CCCCC2)c(OC)c1]

The title compound was prepared from 2,4-dimethoxyphenylacetic acid (1.0 g, 4.7 mmol) following the general procedure outline for amide bond formation. The product was isolated as a yellow oil (690 mg, 56%) following purification by flash column chromatography (EtOAc, Rf=0.6). $^1$H NMR (400 MHz, CDCl$_3$) δ1.38 (m, 2H); 1.52 (m, 2H); 1.58 (m, 2H); 3.36 (m, 2H); 3.56 (m, 2H); 3.20 (s, 2H); 3.29 (s, 3H); 3.81 (s, 3H); 6.45 (m, 3H); 7.13 (d, J=8.6 Hz). $^{13}$C NMR (75 MHz, CDCl$_3$) δ24.46, 25.56, 26.26, 40.72, 40.77, 42.94, 47.27, 111.24, 111.70, 120.66, 127.97, 147.80, 149.07, 169.45. HRMS (ESI+1 ion) m/z calcd for C$_{15}$H$_{22}$NO$_3$ 264.1594, found 264.1605.

2-butyl-2-(2,4-dimethoxy)phenyl-1-(piperidin-1-yl)hexanone

The title compound was prepared following the general procedure outline for α-alkylation from 2-(21,41-dimethyoxy)phenyl-1-(piperidin-1-yl) ethanone (688 mg, 2.61 mmol). The product was isolated as a pale yellow oil (380 mg, 45%) following purification by flash column chromatography (50% EtOAc in hexane, Rf=0.7). $^1$H NMR (400 MHz, CDCl$_3$) δ0.87 (t, J=7 Hz, 3H); 0.973 (m, 1H); 1.13 (m, 1H); 1.23-1.65 (multiple signals, 9H); 2.01 (m, 1H); 3.33 (m, 3H); 3.7 (m, 1H); 3.79 (s, 3H); 3.82 (s, 3H); 4.12 (t, J=7 Hz, 1H); 6.42 (m, 3H); 7.20 (d, J=8 Hz). $^{13}$C NMR (75 MHz, CDCl$_3$) δ14.06, 22.79, 24.73, 25.67, 26.16, 29.92, 34.04, 39.21, 43.11, 46.19, 55.32, 55.50, 98.26, 104.66, 121.93, 128.56, 156.79, 159.38, 172.45. HRMS (ESI+1 ion) m/z calcd for C$_{19}$H$_{30}$NO$_3$ 320.2220, found 320.2229.

Compound 15.6

2-butyl-2-(2,4-dimethyoxy)phenyl-1-(piperidin-1-yl)hexanone

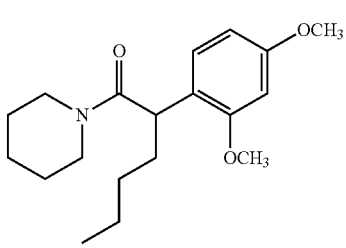

15.6

The title compound was prepared following the general procedure outline for α-alkylation from 2-(2l,4l-dimethyoxy)phenyl-1-(piperidin-1-yl)ethanone (688 mg, 2.61 mmol). The product was isolated as a pale yellow oil (380 mg, 45%) following purification by flash column chromatography (50% EtOAc in hexane, Rf=0.7). $^1$H NMR (400 MHz, CDCl$_3$) δ0.87 (t, J=7 Hz, 3H); 0.97 (m, 1H); 1.13 (m, 1H), 1.23-1.65 (multiple signals, 9H); 2.01 (m, 1H); 3.33 (m, 3H); 3.7 (m, 1H); 3.79 (s, 3H); 3.82 (s, 3H); 4.12 (t, J=7 Hz, 1H); 6.42 (m, 3H); 7.20 (d, J=8 Hz). $^{13}$C NMR (75 MHz, CDCl$_3$) δ14.06, 22.79, 24.73, 25.67, 26.16, 29.92, 34.04, 39.21, 43.11, 46.19, 55.32, 55.50, 98.26, 104.66, 121.93, 128.56, 156.79, 159.38, 172.45. HRMS (ESI+1 ion) m/z calcd for C$_{19}$H$_{30}$NO$_3$ 320.2220, found 320.2229.

Compound 16.2

2-(4-hydroxymethyl)phenyl-1-(piperidin-1-yl)ethanone

The title compound was prepared from 4-hydroxymethylphenylacetic acid (1.0 g, 6.0 mmol) following the general procedure outlined for amide coupling. The product was isolated as a viscous, colourless oil (540 mg, 39%) following purification by flash column chromatography (EtOAc, Rf=0.5). $^1$H NMR (400 MHz, CDCl$_3$) δ1.37 (m, 2H); 1.52 (m, 2H); 1.58 (m, 2H); 3.36 (m, 2H); 3.56 (m, 2H); 3.71 (s, 2H); 4.66 (s, 2H); 7.23 (d, J=8 Hz, 2H); 7.31 (d, J=8 Hz, 2H). $^{13}$C NMR (75 MHz, CDCl$_3$) 524.39, 25.44, 25.47, 26.21, 34.91, 40.77, 42.92, 47.25, 55.77, 64.92, 127.33, 128.76, 134.65, 139.48, 169.30. HRMS (ESI+1 ion) m/z calcd for C$_{14}$H$_{20}$NO$_2$ 234.1489, found 234.1489.

2-(4-tert-butyldimethylsilyloxymethyl)phenyl-1-(piperidin-1-yl)ethanone

To a cooled (0° C.) solution of 2-(4-hydroxymethyl)phenyl-1-(piperidin-1-ypethanone (540 mg, 2.32 mmol) and imidazole (97 mg, 1.4 mmol) in dry DCM was added a solution of TBSCI (214 mg, 1.42 mmol) in DCM (5 mL). The resulting reaction mixture was allowed to stir for 2 hours. After this time, the reaction mixture was washed successively with water (×2) and brine and the organic layer was dried (MgSO$_4$) and concentrated in vacuo. The title compound was obtained as a colourless oil (420 mg, 53%) following purification by flash column chromatography (20% EtOAc, Rf=0.6). $^1$H NMR (400 MHz, CDCl$_3$) δ0.084 (s, 6H); 0.929 (s, 9H); 1.34 (m, 2H); 1.52 (m, 2H); 1.59 (m, 2H); 3.43 (m, 2H); 3.57 (m, 2H); 3.71 (s, 2H); 4.71 (s, 2H); 7.20 (d, J=8 Hz, 2H); 7.25 (d, J=8 Hz, 2H). $^{13}$C NMR (75 MHz, CDCl$_3$) 5-5.21, 24.45, 25.59, 25.97, 26.20, 40.94, 42.89, 47.27, 64.77, 126.41, 128.40, 133.96, 139.81, 169.36. HRMS (ESI+1 ion) m/z calcd for C$_{20}$H$_{34}$NO$_2$Si, 348.2353, found 348.2354.

2-(4-tert-butyldimethylsilyloxymethyl)phenyl-1-(piperidin-1-yl)hexanone

The title compound was prepared from 2-(4-tert-butyldimethylsilyloxymethyl)phenyl-1-(piperidin-1-yl) ethanone (420 mg, 1.21 mmol) following the general procedure outlined for α-alkylation. The product was obtained as a colourless oil (260 mg, 53%) following purification by flash column chromatography (20% EtOAc in hexane, Rf=0.6). $^1$H NMR (400 MHz, CDCl$_3$) δ0.010 (s, 6H); 0.087 (t, J=7 Hz, 314); 0.94 (s, 9H); 1.01 (m, 1H); 1.14 (m, 1H); 1.2-1.6 (multiple signals, 8H); 1.68 (m, 1H); 2.10 (m, 1H); 3.3-3.5 (m, 3H); 3.68 (m, 2H); 4.72 (s, 2H); 7.15 (m, 4H). $^{13}$C NMR (75 MHz, CDCl$_3$) δ−5.20, 14.03, 22.75, 24.75, 25.68, 26.12, 30.40, 34.78, 43.16, 46.62, 48.47, 64.79, 126.38, 127.66, 139.52, 139.73, 171.42. HRMS (ESI+1 ion) m/z calcd for C$_{24}$H$_{42}$NO$_2$Si, 404.2979, found 404.2983.

2-(4-hydroxymethyl)phenyl-1-(piperidin-1-yl)hexanone

A solution of 2-(4-tert-butyldimethylsilyloxymethyl)phenyl-1-(piperidin-1-yl)hexanone (260 mg, 0.64 mmol) in dry THF (5 mL) was added to a flask containing a solution of TBAF in THF (1.29 mmol). The resulting reaction mixture was allowed to stir for 1 hour, by which time analysis by tlc revealed that no starting material remained. The reaction mixture was washed with water (×2) followed by brine and the organic layer was dried (MgSO$_4$) and concentrated in vacuo to afford the crude product. The title compound was isolated as a colourless oil (142 mg, 76%) following purification by flash column chromatography (50% EtOAc in hexane, Rf=0.4). $^1$H NMR (400 MHz, CDCl$_3$) 0.87 (t, J=7 Hz, 3H); 1.04 (m, 1H); 1.14 (m, 1H); 1.9-1.7 (m, 8H); 1.71 (m, 1H); 1.91 (m, 1H); 3.34 (m, 2H); 3.47 (m, 1H); 3.63 (m, 1H); 3.69 (t, J=7 Hz, 1H); 4.66 (s, 2H); 7.25 (d, J=8 Hz, 2H); 7.30 (d, J=8 Hz, 2H). $^{13}$C NMR (75 MHz, CDCl$_3$) 14.02, 22.72, 24.56, 25.57, 26.12, 30.07, 34.76, 43.19, 46.64, 48.41, 65.07, 127.06, 127.99, 139.28, 140.32, 171.32. HRMS (ESI+1 ion) m/z calcd for C$_{18}$H$_{28}$NO$_2$ 290.2114, found 289.2117.

Compound 16.3

2-(4-acetoxymethyl)phenyl-1-(piperidin-1-yl)hexanone

To a round bottomed flask containing DMAP (2 mg) was added a solution of 2-(4-hydroxymethyl) phenyl-1-(piperidin-1-yl)hexanone (30 mg, 0.10 mmol) in dry dichloromethane (2 mL). To the resulting mixture was added dry NEt$_3$ (208 µL, 1.5 mmol) followed by acetic anhydride (100 µL, 1.0 mmol). The resulting mixture was allowed to stir for 3 hours. After this time, the reaction mixture was washed with saturated NaHCO$_3$, water and then brine and the organic phase was dried (Na$_2$SO$_4$) and concentrated under reduced pressure. The title compound was obtained as a colourless oil (20 mg, 60%) following purification by flash column chromatography (50% EtOAc in hexane, Rf=0.7). $^1$H NMR (400 MHz, CDCl$_3$) δ0.86 (t, J=7 Hz, 3H); 1.0-1.2 (2×m, 2H); 1.2-1.5 (multiple signals, 8H); 1.68 (m, 1H); 4.53 (m+s, 4H); 3.33 (m, 1H); 3.39 (m, 1H); 3.49 (m, 1H); 3.60 (m, 1H); 3.70 (t, J=7 Hz, 1H); 5.07 (s, 2H); 7.72 (m, 4H). $^{13}$C NMR (75 MHz, CDCl$_3$) δ14.01, 21.08, 22.72, 24.57, 25.60, 26.20, 30.09, 34.77, 43.20, 46.66, 48.38, 66.07, 128.03, 128.58, 134.24, 141.02, 171.09, 171.17. Note: Compound hydrolyses on standing, HRMS consistent with that of free alcohol.

Compound 17.1

2-(4-methoxyoxyphenyl)-1-(piperidin-1-yl)oct-7-en-1-one

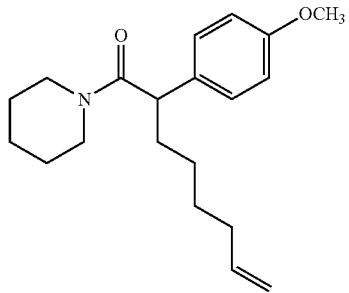

The title compound was prepared following the general procedure for alkylation from 2-(4-hydroxyphenyl)-1-(piperidin-1-yl)ethanone (100 mg, 0.43 mmol) and 6-bromo-1-hexene (70 µL, 0.47 mmol). The purified compound was isolated as a pale yellow oil (26 mg, 26%) following purification by flash column chromatography (20% EtOAc in hexane, Rf=0.5). $^1$H NMR (400 MHz, CDCl$_3$) δ1.1-1.5 (multiple signals, 10H); 1.65 (m, 1H); 2.01 (m, 3H); 3.35, (m, 3H); 3.63 (t, J=7 Hz, 1H); 3.65 (m, 1H); 3.78 (s, 3H); 4.89 (dm, J=10 Hz, 1H); 4.95 (dm, J=17 Hz, 1H); 5.77 (ddd, J=17, 10, 6.5 Hz, 1H); 6.83 (d, J=8.5 Hz, 2H); 7.17 (d, J=8.5 Hz, 2H). $^{13}$C NMR (75 MHz, CDCl$_3$) δ24.69, 25.70, 26.25, 27.46, 29.07, 33.79, 35.02, 43.27, 46.75, 47.88, 55.35, 114.13, 114.34, 278.08, 128.89, 133.05, 139.19, 158.38, 171.69. HRMS (ESI+1 ion) m/z calcd for C$_{20}$H$_{30}$NO$_2$ 316.2271, found 316.2265.

Compound 17.2

2-(4-methoxyphenyl)-N,N-dimethylhexanamide

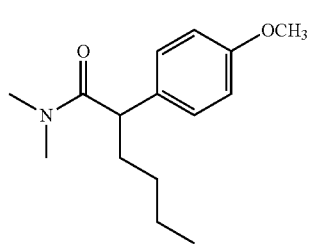

The title compound was prepared following the general procedure for alkylation from 2-(4-hydroxyphenyl)-N,N-dimethylacetamide (100 mg, 0.52 mmol) and 1-bromobutane (70 µL, 0.57 mmol). The purified compound was isolated as a pale yellow oil (120 mg, 60%) following purification by flash column chromatography (EtOAc, Rf=0.7). $^1$H NMR (400 MHz, CDCl$_3$) δ0.85 (t, J=7 Hz, 3H); 1.14 (m, 1H); 1.28 (m, 3H); 1.68 (m, 1H); 2.05 (m, 1H); 2.93 (s, 3H); 2.94 (s, 3H); 3.63 (t, J=7 Hz, 1H); 3.78 (s, 3H); 6.84 (d, J=8.8 Hz, 2H); 7.20 (d, J=8.8 Hz, 2H). $^{13}$C NMR (75 MHz, CDCl$_3$) δ14.16, 22.84, 35.03, 36.02, 37.30, 48.09, 55.37, 114.14, 129.04, 132.64, 158.50, 173.75. HRMS (ESI+1 ion) m/z calcd for C$_{16}$H$_{24}$NO$_2$ 262.1802, found 262.1795.

Compound 17.3

2-(4-methoxyphenyl)-N,N-dimethyloct-7-enamide

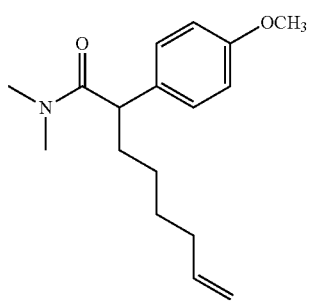

The title compound was prepared following the general procedure for alkylation from 2-(4-hydroxyphenyl)-N,N-dimethylacetamide (100 mg, 0.52 mmol) and 6-bromo-1-hexene (84 µL, 0.57 mmol). The purified compound was isolated as a pale yellow oil (120 mg, 60%) following purification by flash column chromatography (EtOAc, Rf=0.6). $^1$H NMR (400 MHz, CDCl$_3$) δ1.1-1.5 (multiple signals, 4H); 1.66 (m, 1H); 2.02 (m, 3H); 2.93 (2×s, 6H); 3.63 (t, J=7 Hz, 1H); 3.78 (s, 3H); 4.90 (dm, J=10 Hz, 1H); 4.96 (dm, J=17 Hz, 1H); 5.77 (ddd, J=17, 10, 6.5 Hz, 1H); 6.85 (d, J=8.8 Hz, 2H); 7.19 (d, J=8.8 Hz, 2H). $^{13}$C NMR (75 MHz, CDCl$_3$) δ27.41, 29.02, 33.75, 35.10, 36.00, 37.27, 48.05, 55.34, 114.13, 114.35, 128.98, 132.49, 139.12, 158.49, 173.62. HRMS (ESI+1 ion) m/z calcd for C$_{17}$H$_{26}$NO$_2$ 276.1958, found 276.1958.

Compound 16.5

2-(4-hydroxyphenyl)-1-(piperidin-1-yl)hexan-1-one

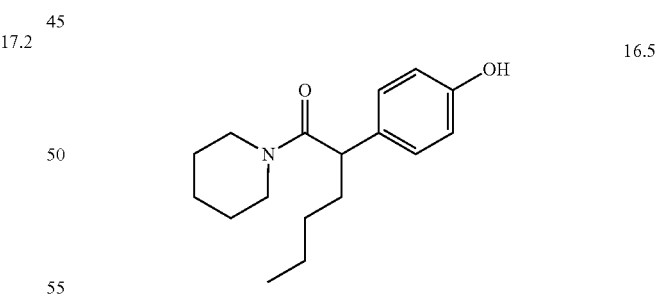

To a cooled (−78° C.) solution of 15.1 (1 g, 3.46 mmol) in dry DCM was added a solution of boron tribromide in DCM (10 mL, 10 mmol). The resulting mixture was allowed to warm to room temperature over a number of hours (at least 3) and continued stirring for a further 14 hours (17 hours in total). The reaction was quenched by the careful dropwise addition of ammonium hydroxide to the reaction mixture (caution: slow addition to reaction mixture at 0° C.). Following this, water was added to the reaction mixture and the aqueous phase removed. The organic layer was dried (MgSO$_4$) and concentrated in vacuo. The title compound was obtained as a pale brown solid (0.93 g, 97%). ¹H NMR (400 MHz, CDCl₃) δ0.85 (t, 3H); 1.29 (m, 10H); 1.70 (m, 2H); 2.04 (m, 1H); 3.39 (m, 2H); 3.63 (t, 1H); 3.67 (m, 1H); 6.77 (d, J=8.5 Hz, 2H); 7.12 (d, J=8.5 Hz, 2H). ¹³C NMR (75 MHz, CDCl₃) δ13.99, 22.67, 24.51, 25.55, 26.11, 29.98, 34.59, 43.32, 46.75, 47.73, 115.63, 128.83, 132.28, 154.95, 172.09. HRMS (ESI+1 ion) m/z calcd for $C_{17}H_{26}NO_2$ 276.1958, found 276.1954.

Compound 17.7

2-(4-hydroxyphenyl)-N,N-dimethylhexanamide

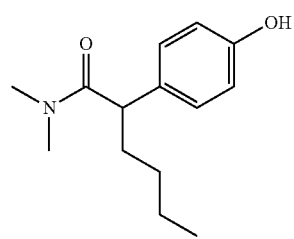

17.7

The title compound was obtained as a pale yellow solid (6 mg, 53%) in a similar manner to that described for 16.5 from 17.2 (12 mg, 0.048 mmol). δ0.85 (t, J=7 Hz, 3H); 1.1-1.5 (multiple signals, 4H); 1.65 (m, 1H); 2.03 (m, 1H); 2.94 (s, 3H); 3.63 (t, J=7 Hz, 1H); 6.76 (d, J=8.5 Hz, 2H); 7.16 (d, J=8.5 Hz, 2H). ¹³C NMR (75 MHz, CDCl₃) δ14.15, 22.82, 30.14, 31.10, 34.96, 48.05, 115.61, 129.22, 132.53, 154.65, 173.87. HRMS (ESI+1 ion) m/z calcd for $C_{14}H_{23}NO_2$ 236.1645, found 236.1644.

Compound 17.8

2-(4-hydroxyphenyl)-N,N-dimethyloct-7-enamide

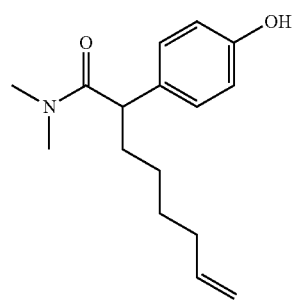

17.8

To a cooled (−78° C.) solution of 17.3 (25 mg, 0.09 mmol) in dry CH₂Cl₂ (1 mL) was added BBr₃ (1 M solution in CH₂Cl₂, 0.27 mL, 0.27 mmol). The resulting mixture was allowed to warm to room temperature and was stirred for an additional 30 minutes. After this time, the reaction mixture was cooled to −78° C. and MeOH (2 mL) was added to the reaction mixture. After 5 minutes the resulting mixture was poured onto water and an additional 10 mL of CH₂Cl₂ was added. The organic layer was washed dried and concentrated in vacuo to afford the crude product as a pale yellow solid. Purification of the crude product by flash column chromatography (50% EtOAc/hexane, Rf=0.2) afforded the title compound as a pale yellow oil which solidified upon standing (4 mg, 15%). ¹H NMR (400 MHz, CDCl₃) δ1.1-1.5 (multiple signals, 4H); 1.67 (m, 1H); 1.98 (m, 3H); 2.93 (s, 3H); 2.94 (s, 3H); 3.62 (t, J=7 Hz, 1H); 4.84 (s, 1H ArOH); 4.90 (dm, J=10 Hz, 1H); 4.95 (dm, J=17 Hz, 1H); 5.77 (ddd, J=17, 10, 6.5 Hz, 1H); 6.76 (d, J=8.8 Hz, 2H); 7.14 (d, J=8.8 Hz, 2H). ¹³C NMR (75 MHz, CDCl₃) δ27.29, 28.90, 33.64, 34.97, 35.94, 37.19, 47.92, 114.26, 115.51, 129.10, 132.48, 139.01, 173.55. HRMS (ESI+1 ion) m/z calcd for $C_{16}H_{24}NO_2$ 262.1802, found 262.1086.

Compound 17.6

2-(4-hydroxyphenyl)-1-(piperidin-1-yl)oct-7-en-1-one

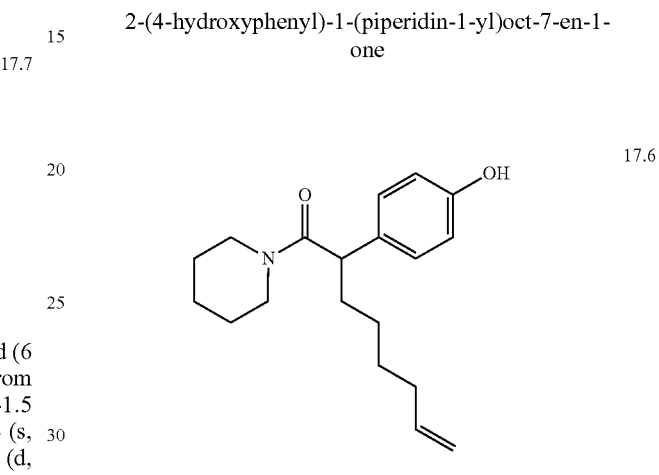

17.6

The title compound was prepared in a similar manner to that described for 17.8 from 2-(4-methoxyoxyphenyl)-1-(piperidin-1-yl)oct-7-en-1-one (50 mg, 0.18 mmol). The title compound was obtained as a colourless, low melting point solid (6 mg, 11%) following purification by flash column chromatography (50% EtOAc/hexane, Rf=0.5). ¹H NMR (400 MHz, CDCl₃) δ1.0-1.5 (multiple signals, 10H); 1.66 (m, 1H); 2.02 (m, 3H); 3.38, (m, 3H); 3.62 (t, J=7 Hz, 1H); 3.65 (m, 1H); 4.88 (dm, J=10 Hz, 1H); 4.95 (dm, J=17 Hz, 1H); 5.76 (ddd, J=17, 10, 6.5 Hz, 1H); 6.76 (d, J=8.5 Hz, 2H); 7.11 (d, J=8.5 Hz, 2H). ¹³C NMR (75 MHz, CDCl₃) δ24.54, 25.58, 26.12, 27.31, 28.91, 33.66, 34.79, 43.27, 46.72, 47.72, 114.24, 115.59, 128.92, 132.59, 139.04, 154.64, 171.80. HRMS (ESI+1 ion) m/z calcd for $C_{19}H_{28}NO_2$ 302.2115, found 302.2120.

2-(4-hydroxymethyl)phenyl-1-(piperidin-1-yl)ethanone

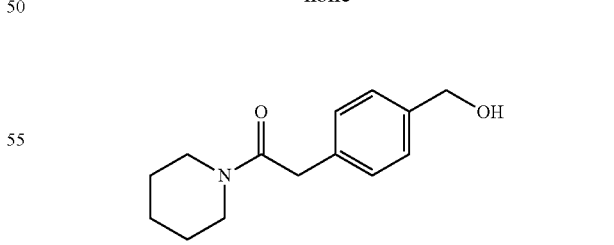

The title compound was prepared from 4-hydroxymethylphenylacetic acid (1.0 g, 6.0 mmol) following the general procedure outlined for DCC mediated amide formation. The product was isolated as a viscous, colourless oil (0.54 g, 39%) following purification by flash column chromatography (EtOAc, Rf=0.5). ¹H NMR (400 MHz, CDCl₃) δ1.37 (m, 2H); 1.52 (m, 2H); 1.58 (m, 2H); 3.36 (m, 2H); 3.56 (m, 2H); 3.71 (s, 2H); 4.66 (s, 2H); 7.23 (d, J=8 Hz, 2H); 7.31 (d, J=8 Hz, 2H). $^{13}$C NMR (75 MHz, CDCl$_3$) δ24.39, 25.44, 25.47, 26.21, 34.91, 40.77, 42.92, 47.25, 55.77, 64.92, 127.33, 128.76, 134.65, 139.48, 169.30. HRMS (ESI+1 ion) m/z calcd for C$_{14}$H$_{20}$NO$_2$ 234.1489, found 234.1489.

2-(4-tert-butyldimethylsilyloxymethyl)phenyl-1-(piperidin-1-yl)ethanone

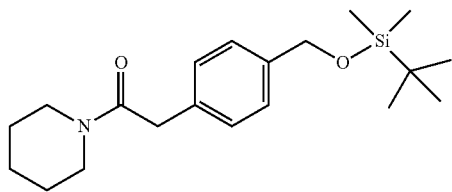 [SMILES: CC(C)(C)[Si](C)(C)OCc1ccc(CC(=O)N2CCCCC2)cc1]

To a cooled (0° C.) solution of 2-(4-hydroxymethyl) phenyl-1-(piperidin-1-yl)ethanone (540 mg, 2.32 mmol) and imidazole (97 mg, 1.4 mmol) in dry DCM was added a solution of TBSCl (214 mg, 1.42 mmol) in DCM (5 mL). The resulting reaction mixture was allowed to stir for 2 hours. After this time, the reaction mixture was washed successively with water (×2) and brine and the organic layer was dried (MgSO$_4$) and concentrated in vacuo. The title compound was obtained as a colourless oil (420 mg, 53%) following purification by flash column chromatography (20% EtOAc, Rf=0.6). $^1$H NMR (400 MHz, CDCl$_3$) δ0.084 (s, 6H); 0.929 (s, 9H); 1.34 (m, 2H); 1.52 (m, 2H); 1.59 (m, 2H); 3.43 (m, 2H); 3.57 (m, 2H); 3.71 (s, 2H); 4.71 (s, 2H); 7.20 (d, J=8 Hz, 2H); 7.25 (d, J=8 Hz, 2H). $^{13}$C NMR (75 MHz, CDCl$_3$) δ-5.21, 24.45, 25.59, 25.97, 26.20, 40.94, 42.89, 47.27, 64.77, 126.41, 128.40, 133.96, 139.81, 169.36. HRMS (ESI+1 ion) m/z calcd for C$_{20}$H$_{34}$NO$_2$Si, 348.2353, found 348.2354.

2-(4-tert-butyldimethylsilyloxymethyl)phenyl-1-(piperidin-1-yl)hexanone

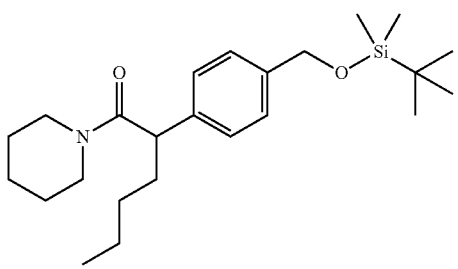 [SMILES: CCCCC(C(=O)N1CCCCC1)c1ccc(CO[Si](C)(C)C(C)(C)C)cc1]

The title compound was prepared from 2-(4-tert-butyldimethylsilyloxymethyl)phenyl-1-(piperidin-1-yl) ethanone (420 mg, 1.21 mmol) following the general procedure outlined for α-alkylation. The product was obtained as a colourless oil (260 mg, 53%) following purification by flash column chromatography (20% EtOAc in hexane, Rf=0.6). $^1$H NMR (400 MHz, CDCl$_3$) δ0.010 (s, 6H); 0.087 (t, J=7 Hz, 3H); 0.94 (s, 9H); 1.01 (m, 1H); 1.14 (m, 1H); 1.2-1.6 (multiple signals, 8H); 1.68 (m, 1H); 2.10 (m, 1H); 3.3-3.5 (m, 3H); 3.68 (m, 2H); 4.72 (s, 2H); 7.15 (m, 4H). $^{13}$C NMR (75 MHz, CDCl$_3$) δ-5.20, 14.03, 22.75, 24.75, 25.68, 26.12, 30.40, 34.78, 43.16, 46.62, 48.47, 64.79, 126.38, 127.66, 139.52, 139.73, 171.42. HRMS (ESI+1 ion) m/z calcd for C$_{24}$H$_{42}$NO$_2$Si, 404.2979, found 404.2983.

Compound 16.1

2-(4-hydroxymethyl)phenyl-1-(piperidin-1-yl)hexanone

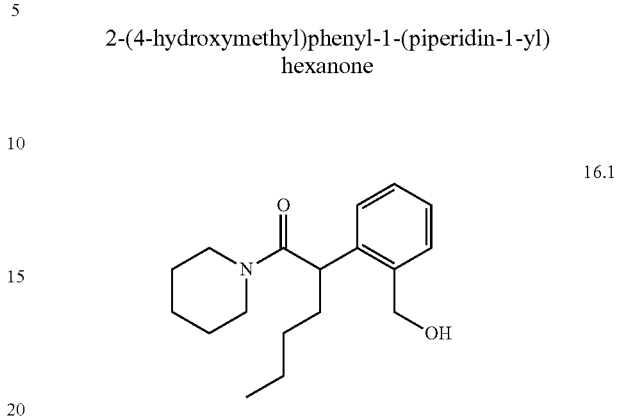

16.1

A solution of 2-(4-tert-butyldimethylsilyloxymethyl)phenyl-1-(piperidin-1-yl)hexanone (260 mg, 0.64 mmol) in dry THF (5 mL) was added to a flask containing a solution of TBAF in THF (1.29 mmol). The resulting reaction mixture was allowed to stir for 1 hour, by which time analysis by tlc revealed that no starting material remained. The reaction mixture was washed with water (×2) followed by brine and the organic layer was dried (MgSO$_4$) and concentrated in vacuo to afford the crude product. The title compound was isolated as a colourless oil (142 mg, 76%) following purification by flash column chromatography (50% EtOAc in hexane, Rf=0.4). $^1$H NMR (400 MHz, CDCl$_3$) δ0.87 (t, J=7 Hz, 3H); 1.04 (m, 1H); 1.14 (m, 1H); 1.9-1.7 (m, 8H); 1.71 (m, 1H); 1.91 (m, 1H); 3.34 (m, 2H); 3.47 (m, 1H); 3.63 (m, 1H); 3.69 (t, J=7 Hz, 1H); 4.66 (s, 2H); 7.25 (d, J=8 Hz, 2H); 7.30 (d, J=8 Hz, 2H). $^{13}$C NMR (75 MHz, CDCl$_3$) δ14.02, 22.72, 24.56, 25.57, 26.12, 30.07, 34.76, 43.19, 46.64, 48.41, 65.07, 127.06, 127.99, 139.28, 140.32, 171.32. HRMS (ESI+1 ion) m/z calcd for C$_{18}$H$_{28}$NO$_2$ 290.2114, found 289.2117.

Compound 16.3

2-(4-acetoxymethyl)phenyl-1-(piperidin-1-yl)hexanone

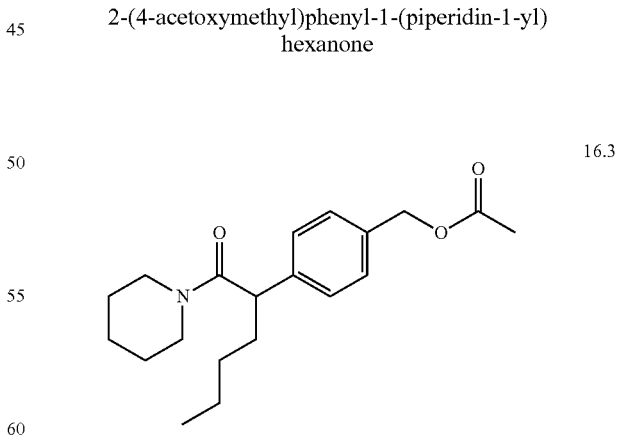

16.3

To a round bottomed flask containing DMAP (2 mg) was added a solution of 2-(4-hydroxymethyl) phenyl-1-(piperidin-1-yl)hexanone (30 mg, 0.10 mmol) in dry CH$_2$Cl$_2$ (2 mL). To the resulting mixture was added dry NEt$_3$ (208 μL, 1.5 mmol) followed by acetic anhydride (100 μL, 1.0 mmol). The resulting mixture was allowed to stir for 3 hours. After this time, the reaction mixture was washed with saturated NaHCO$_3$, water and then brine and the organic phase was dried (Na$_2$SO$_4$) and concentrated under reduced pressure. The title compound was obtained as a colourless oil (20 mg, 60%) following purification by flash column chromatography (50% EtOAc in hexane, Rf=0.7). $^1$H NMR (400 MHz, CDCl$_3$) δ0.86 (t, J=7 Hz, 3H); 1.0-1.2 (2×m, 2H); 1.2-1.5 (multiple signals, 8H); 1.68 (m, 1H); 4.53 (m+s, 4H); 3.33 (m, 1H); 3.39 (m, 1H); 3.49 (m, 1H); 3.60 (m, 1H); 3.70 (t, J=7 Hz, 1H); 5.07 (s, 2H); 7.72 (m, 4H). $^{13}$C NMR (75 MHz, CDCl$_3$) δ14.01, 21.08, 22.72, 24.57, 25.60, 26.20, 30.09, 34.77, 43.20, 46.66, 48.38, 66.07, 128.03, 128.58, 134.24, 141.02, 171.09, 171.17. Note: Compound hydrolyses on standing, HRMS consistent with that of free alcohol.

Compound 16.11

4-(1-oxo-1-(piperidin-1-yl)hexan-2-yl)phenyl acrylate

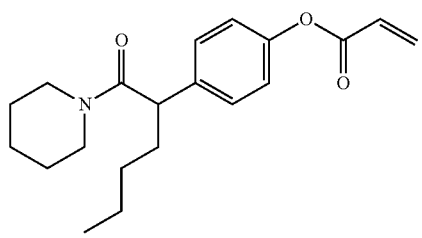

16.11

To a cooled (0° C.) stirred solution of 16.5 (100 mg, 0.36 mmol) and triethylamine (56 μL, 0.40 mmol) in dry CH$_2$Cl$_2$ (10 mL) was added acryloyl chloride (33 μL, 0.40 mmol). The resulting mixture was allowed to warm to room temperature and was stirred for a further 1 hour, by which time analysis by tlc (50% EtOAc/hexane) revealed complete consumption of starting material. After this time, the reaction mixture was concentrated in vacuo and purified by flash column chromatography (50% EtOAc/hexane, Rf=0.5) to afford the title compound as a colourless oil (120 mg, >95%). $^1$H NMR (400 MHz, CDCl$_3$) (δ0.85 (t, J=7 Hz, 3H); 1.0-1.6 (multiple signals, 10H); 1.70 (m, 1H); 2.05 (m, 1H); 3.3-3.5 (2×m, 3H); 3.68 (m, 1H); 3.70 (t, J=7 Hz, 1H); 5.99, (d, J=10 Hz, 1H); 6.29 (dd, J=17, 10 Hz, 1H); 6.57 (d, J=17 Hz, 1H); 7.06 (d, J=8.4 Hz, 2H); 7.28 (d, J=8.4 Hz, 2H). $^{13}$C NMR (75 MHz, CDCl$_3$) δ13.93, 22.63, 24.49, 25.51, 26.10, 30.00, 34.77, 43.12, 46.61, 47.96, 121.53, 127.88, 128.69, 132.42, 138.42, 149.15, 164.43, 171.06. HRMS (ESI+1 ion) m/z calcd for C$_{20}$H$_{28}$NO$_3$ 330.1989, found 330.2056.

Compound 16.4

4-(1-oxo-1-(piperidin-1-yl)hexan-2-yl)phenyl acetate

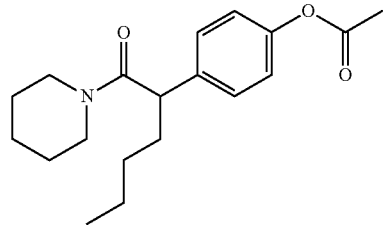

16.4

Acetic anhydride (38 μL, 0.40 mmol) as added to a cooled (0° C.) stirred solution of 16.5 (100 mg, 0.36 mmol) and pyridine (32 μL, 0.40 mmol) in dry CH$_2$Cl$_2$ (20 mL). The reaction was allowed to warm to room temperature and stirring was continued for a further 18 hours, by which time analysis by tlc (50% EtOAc/hexane) showed consumption of starting material. The crude reaction mixture was washed with dilute (0.1 M) HCl followed by water. The organic layer was dried (MgSO$_4$) and concentrated in vacuo and the resulting oily residue was purified by flash column chromatography (50% EtOAc/hexane, Rf=0.26) to afford the title compound as a colourless oil (110 mg, >95%). $^1$H NMR (400 MHz, CDCl$_3$) δ0.86 (t, J=7 Hz, 3H); 1.0-1.7 (multiple signals, 11H); 2.1 (m, 1H); 2.28 (s, 3H); 3.37 (m, 2H); 3.48 (m, 1H); 3.59 (m, 1H); 3.72 (t, J=7 Hz, 1H); 7.04 (d, J=8.4 Hz, 2H); 7.28 (d, J=8.4 Hz, 2H). $^{13}$C NMR (75 MHz, CDCl$_3$) δ13.96, 21.14, 22.67, 24.53, 25.55, 26.15, 30.04, 34.80, 43.15, 46.64, 47.97, 121.59, 128.72, 138.38, 149.29, 169.39, 171.11. HRMS (ESI+1 ion) m/z calcd for C$_{19}$H$_{28}$NO$_3$ 318.2064, found 318.2060.

Compound 16.6

2-(4-(2-hydroxyethoxy)phenyl)-1-(piperidin-1-yl)hexan-1-one

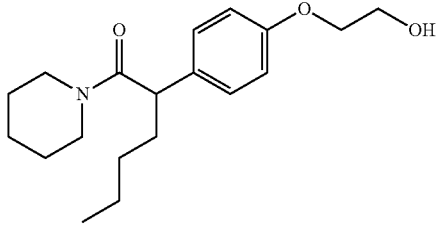

16.6

A solution of 16.5 (0.50 g, 1.8 mmol) ethylene carbonate (176 mg, 2.00 mmol) and tetraethylammonium bromide (20 mg, 0.09 mmol) in dry DMF (10 mL) was heated at an oil bath temperature of 180° C. for 16 hours. After this time cold water (50 mL) was added and the resulting mixture was extracted with EtOAc (3×20 ml). The combined organic layers were washed with water, dried (MgSO$_4$) and concentrated in vacuo. The crude product was purified was purified by flash column chromatography (10% MeOH in CH$_2$Cl$_2$, Rf=0.4) to afford the title compound as a colourless oil (200 mg, 34%). $^1$H NMR (400 MHz, CDCl$_3$) δ0.84 (t, J=7 Hz, 3H); 1.05 (m, 1H); 1.17 (m, 1H); 1.2-1.6 (multiple signals, 8H); 1.7 (m, 1H); 2.08 (m, 1H); 2.39 (t, J=6 Hz, 1H (OH)); 3.35 (m, 3H); 3.62 (t, J=7 Hz, 1H); 3.64 (m, 1H); 3.92 (m, 2H); 4.05 (m, 1H); 6.83 (d, J=8.4 Hz, 2H); 7.16 (d, J=8.4 Hz, 2H). $^{13}$C NMR (75 MHz, CDCl$_3$) δ13.96, 22.64, 24.50, 25.51, 26.09, 29.96, 34.70, 43.10, 46.58, 47.70, 61.36, 69.10, 114.59, 128.78, 133.38, 157.28, 171.55. HRMS (ESI+1 ion) m/z calcd for C$_{19}$H$_{30}$NO$_3$ 320.2220, found 320.2205.

Compound 16.8

2-(4-(1-oxo-1-(piperidin-1-yl)hexan-2-yl)phenoxy) ethyl acetate

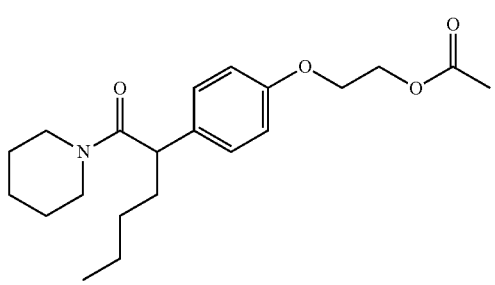

16.8

To a cooled (0° C.) stirred solution of 16.6 (100 mg, 0.31 mmol) and DMAP (85 mg, 0.34 mmol) in dry $CH_2Cl_2$ (20 mL) was added acetyl chloride (50 μL, 0.34 mmol). The resulting reaction mixture was stirred at reflux for 16 hours by which time analysis by tlc (50% EtOAc/hexane) showed complete consumption of starting material. The reaction mixture was washed with HCl (0.1 M) and water and the organic layer was dried ($MgSO_4$) and concentrated in vacuo. The title compound was obtained as a colourless oil (110 mg, >95% yield) following purification by flash column chromatography (50% EtOAc/hexane, Rf=0.4). $^1$H NMR (400 MHz, $CDCl_3$) δ0.85 (t, J=7 Hz, 3H); 1.05-1.60 (multiple signals, 10H); 1.7 (m, 1H); 2.08 (m, 1H); 2.10 (s, 3H); 3.35-3.45 (m, 3H); 3.6-3.7 (m, 2H); 4.15 (app t, J=5 Hz, 2H); 4.40 (app t, J=5 Hz, 2H); 6.84 (d, J=8.4 Hz, 2H); 7.17 (d, J=8.4 Hz, 2H). $^{13}$C NMR (75 MHz, $CDCl_3$) δ13.99, 20.89, 22.69, 24.55, 25.56, 26.15, 30.11, 34.77, 43.11, 46.61, 47.74, 62.86, 65.88, 114.68, 128.85, 133.61, 157.13, 171.00, 171.55. HRMS (ESI+1 ion) m/z calcd for $C_{21}H_{32}NC_4$ 362.2326, found 362.2320.

Compound 16.7

Methyl 2-(4-(1-oxo-1-(piperidin-1-yl)hexan-2-yl) phenoxy)acetate

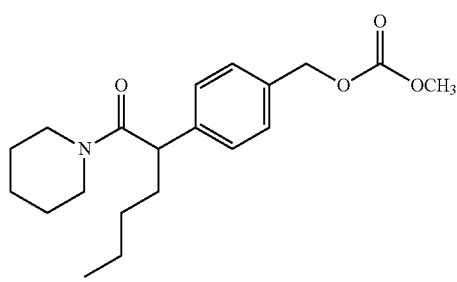

16.7

To a stirred solution of 16.5 (300 mg, 1.15 mmol) and $K_2CO_3$ (400 mg, 2.87 mmol) in dry acetonitrile (20 mL) was added methylbromoacetate (0.18 g, 1.2 mmol). The resulting mixture was refluxed for 16 hours by which time analysis by tlc (5% MeOH in $CH_2Cl_2$) showed that no starting material remained. Acetonitrile was removed in vacuo and the residue was taken up in EtOAc and washed with water. The organic layer was dried ($MgSO_4$) and concentrated in vacuo and the title compounds was obtained as a colourless oil (300 mg, 72%) following purification by flash column chromatography (5% MeOH in $CH_2Cl_2$, Rf=0.7). $^1$H NMR (400 MHz, $CDCl_3$) δ0.86 (t, J=7 Hz, 3H); 1.05-1.60 (multiple signals, 10H); 1.7 (m, 1H); 2.05 (m, 1H); 3.38 (m, 2H); 3.42 (m, 1H), 3.6-3.7 (m, 2H); 3.80 (s, 3H); 4.61 (s, 2H); 6.83 (d, J=8.4 Hz, 2H); 7.19 (d, J=8.4 Hz, 2H). $^{13}$C NMR (75 MHz, $CDCl_3$) δ14.02, 22.72, 24.59, 25.60, 26.18, 30.06, 34.78, 43.15, 46.65, 47.73, 52.26, 65.45, 114.80, 128.94, 134.29, 156.51, 169.44, 171.48. HRMS (ESI+1 ion) m/z calcd for $C_{20}H_{30}NO_4$ 348.2169, found 348.2157.

Compound 16.9

2-(4-(1-oxo-1-(piperidin-1-yl)hexan-2-yl)phenoxy) acetic acid

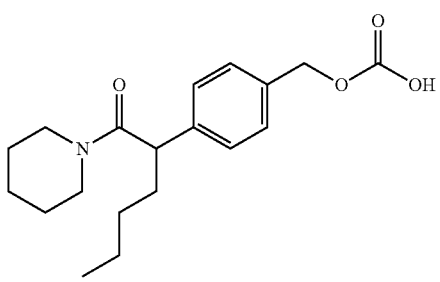

16.9

Powdered LiOH (72 mg, 3.0 mmol) was added to a solution of 16.7 (100 mg, 0.30 mmol) in THF (10 mL) and the mixture was allowed to stir at room temperature for 16 hours. After this time the reaction mixture was acidified with HCl (0.1 M) and washed with EtOAc (3×20 mL). The organic phase was dried ($MgSO_4$) and concentrated in vacuo. The title compound was obtained as a colourless oil (59 mg, 60%) following purification by flash column chromatography (10% MeOH in $CH_2Cl_2$, Rf=0.5). $^1$H NMR (400 MHz, $CDCl_3$) δ0.84 (t, J=7 Hz, 3H); 1.05-1.60 (multiple signals, 10H); 1.68 (m, 1H); 2.05 (m, 1H); 3.37 (m, 2H); 3.42 (m, 1H), 3.66 (m, 2H); 4.63 (s, 2H); 6.85 (d, J=8.4 Hz, 2H); 7.18 (d, J=8.4 Hz, 2H). $^{13}$C NMR (75 MHz, $CDCl_3$) δ13.96, 22.61, 24.41, 25.52, 26.10, 29.92, 34.52, 43.49, 46.82, 47.71, 65.10, 114.87, 128.89, 133.87, 156.46, 171.92, 172.03. HRMS (ESI+1 ion) m/z calcd for $C_{19}H_{28}NC_4$ 334.2013, found 334.2001.

Compound 16.10

1-(piperidin-1-yl)-2-(4-(2-(trimethylsilyi)ethoxy) phenyl)hexan-1-one

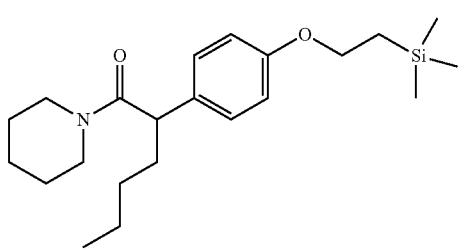

16.10

To cooled (0° C.) solution of 16.5 (100 mg, 0.36 mmol), triphenylphosphine (140 mg, 0.54 mmol) and trimethylsilylethanol (80 μL, 0.54 mmol) in dry THF (10 mL) was added DIAD (110 μL) over a period of 10 minutes. The resulting reaction mixture was allowed to warm to room temperature and was stirred for a further 16 hours. After this time, the solvent was removed in vacuo and the residue was taken up in EtOAc and washed with water. The organic layer was dried (MgSO$_4$) and concentrated in vacuo and the resulting residue was purified by flash column chromatography (50% EtOActhexane, Rf=0.7) to afford the title compound as a pale yellow oil (40 mg, 30%). $^1$H NMR (400 MHz, CDCl$_3$) δ0.07 (s, 9H); 0.84 (t, J=7 Hz, 3H); 1.05 (m, 1H); 1.17 (m, 1H); 1.2-1.6 (multiple signals, 10H; app t, J=6 Hz, 2H); 1.7 (m, 1H); 2.05 (m, 1H); 3.25-3.35 (m, 3H); 3.62 (t, J=7 Hz, 1H); 3.65 (m, 1H); 4.03 (app t, J=6 Hz, 2H); 4.05 (m, 1H); 6.80 (d, J=8.4 Hz, 2H); 7.15 (d, J=8.4 Hz, 2H). $^{13}$C NMR (75 MHz, CDCl$_3$) δ-1.33, 14.01, 17.75, 22.71, 24.58, 25.57, 26.11, 30.03, 34.77, 43.11, 46.60, 47.80, 65.31, 114.59, 128.70, 132.75, 157.59, 171.67. HRMS (ESI+1 ion) m/z calcd for C$_{22}$H$_{38}$NO$_2$ 376.2672, found 376.2666.

4-(1-oxo-1-(piperidin-1-yl)hexan-2-yl)benzaldehyde

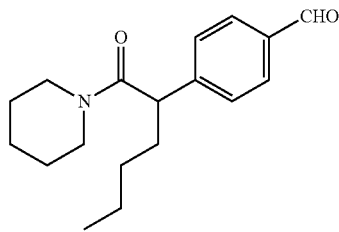 [SMILES: CCCCC(C(=O)N1CCCCC1)c1ccc(C=O)cc1]

DMSO (0.20 mL, 2.8 mmol) was added to a cooled (−78° C.) stirred solution of oxaloyl chloride (122 μL, 1.42 mmol) in dry CH$_2$Cl$_2$ (5 mL). After 5 minutes 16.2 (300 mg, 1.29 mmol) was added and stirring was continued for 15 minutes after which time triethylamine (0.90 mL, 6.5 mmol) was added dropwise. After a further 5 minutes, the mixture was allowed to warm to room temperature. The reaction mixture was washed with HCl (0.1 M) and the organic layer was further extracted with water, dried (MgSO$_4$) and concentrated in vacuo. The title compound was obtained as a colourless oil (222 mg, 59%). No purification was necessary. $^1$H NMR (400 MHz, CDCl$_3$) δ0.80 (t, J=7 Hz, 3H); 1.05 (m, 1H); 1.15 (m, 1H); 1.2-1.6 (multiple signals, 8H); 1.7 (m, 1H); 2.05 (m, 1H); 3.29 (m, 2H); 3.36 (m, 1H); 3.61 (m, 1H); 3.71 (t, J=7 Hz, 1H); 7.39 (d, J=8.4 Hz, 2H); 7.76 (d, J=8.4 Hz, 2H). $^{13}$C NMR (75 MHz, CDCl$_3$) δ13.97, 22.67, 24.49, 25.55, 26.21, 30.05, 34.64, 43.33, 46.69, 48.88, 128.57, 130.21, 135.08, 148.03, 170.36, 191.91. HRMS (ESI+1 ion) miz calcd for C$_{18}$H$_{26}$NO$_2$ 288.1958, found 288.1963.

Compound 17.9

4-(1-oxo-1-(piperidin-1-yl)hexan-2-yl)benzoic acid 17.9

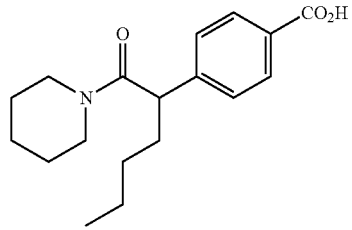

Oxone (257 mg, 0.42 mmol) was added to a stirred solution of 4-(1-oxo-1-(piperidin-1-yl) hexan-2-yl)benzaldehyde (100 mg, 0.35 mmol) in DMF (5 mL) and the resulting mixture was stirred at room temperature for 16 hours. The DMF was removed in vacuo and the resulting residue was purified by flash column chromatography (50% EtOAc/hexane, Rf=0.4) to afford the desired compound as a pale yellow solid (68 mg, 64%). MP=142° C. $^1$H NMR (400 MHz, CDCl$_3$) δ0.86 (t, J=7 Hz, 3H); 1.05 (m, 1H); 1.15 (m, 1H); 1.2-1.6 (multiple signals, 8H); 1.71 (m, 1H); 2.10 (m, 1H); 3.33-3.43 (m, 3H); 3.69 (m, 1H); 3.77 (t, J=7 Hz, 1H); 7.38 (d, J=8.4 Hz, 2H); 8.02 (d, J=8.4 Hz, 2H). $^{13}$C NMR (75 MHz, CDCl$_3$) δ13.98, 22.68, 24.50, 25.55, 26.16, 30.04, 34.60, 43.32, 46.68, 48.82, 128.04, 130.50, 153.75, 170.59. HRMS (ESI+ ion) m/z calcd for C$_{18}$H$_{26}$NO$_3$ 304.1907, found 304.1917.

The remaining compounds were made by methods corresponding to those given above, with appropriate variation of starting materials.

Examples Part 2—Polymer Systems

A number of polymers were synthesised, which polymers included a pendant group corresponding to antifouling compound 16.5.

Specifically, compound 16.5 was incorporated into acrylate based polymers via the use of monomer 16.11.

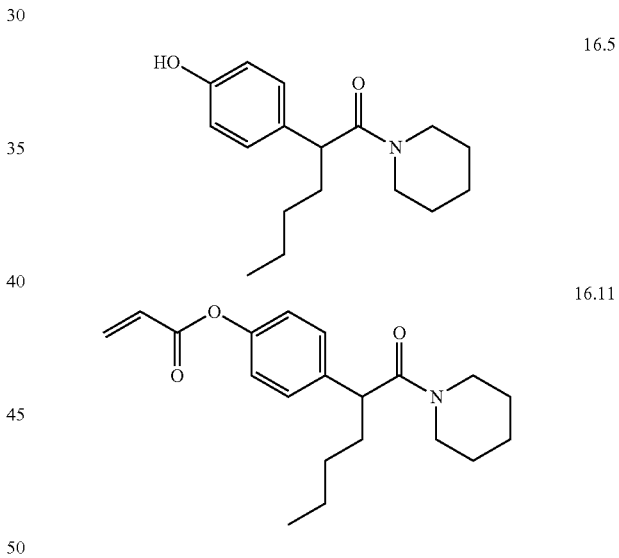

The polymers were evaluated with respect to their ability to release (active) compound 16.5 in an aqueous environment in a sustained fashion. In particular, the antifouling efficacy of polymeric materials was studied in laboratory and field assays to identify anti-fouling performance and toxicity.

Synthesis of Polymers

The same polymers were designed and synthesized as the embodiments to illustrate the potential applications of our invention in marine coatings. But no limitations should be drawn from these embodiments.

Polymers containing compound 16.5 as a releasable functional unit were designed with moderately hydrophilic (to ensure hydration in water) and to possess suitable strength, solubility and compatibility with commercial marine paints. To fulfil these requirements, the Tg of the polymer should preferably be higher than room temperature and the molecular weight is targeted to be approximately 10 KDaltons.

Such polymers were synthesized by the polymerization of vinyl-containing compound 16.11 with the appropriate vinyl monomers under free radical conditions using AIBN, ABCN or benzoyl peroxide as initiators.

Polymer A

P(16.11-co-MMA-co-HEA) The copolymer of compound 16.11 with methyl methacrylate (MMA) and hydroxyethyl acrylate (HEA) was designed to obtain the functional polymer. Thus 16.11, methyl methacrylate (MMA) and (HEA) were mixed and polymerized under standard free radical conditions.

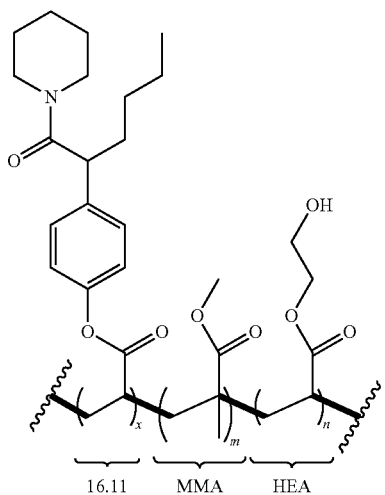

Polymer A

The mass ratio was designed so that MMA would form the majority of the backbone of the polymer, imparting mechanical strength and ensuring a Tg higher than room temperature, whilst HEA would provide hydrogen bonding capabilities which can improve the hydrophilicity of the polymer.

0.54 g of the functional monomer (16.11) (heavy viscose oil-like yellow liquid) was mixed with 2.0 g of MMA, 1.0 g of 2-hydroxylehtyl acrylate (HEA) and 40 mg of ABCN in 3 ml of DMF. The mixture was degassed by purging with nitrogen for 10 min. and then placed into an oil bath thermosetted at 70° C. for 16 hours. Following this, the reaction mixture was poured into 50 mL of ether. The precipitate was collected by filtration and dried under vacuum at room temperature to afford the title compounds as a colourless solid (2.5 g, 74%).

Analysis of the polymeric material by IR spectroscopy revealed the expected ester C=O stretching absorbances at ~1730 $cm^{-1}$ along with a key absorbance detected at 1621 $cm^{-1}$. Such low frequency C=O vibrations are characteristic of tertiary amides, and therefore this band is assigned to the piperidine amide linkage of the polymerized 16.11.

Polymer B

P(16.11-co-MMA-co-VP)

Polymer B was of a similar design to polymer A but vinyl pyrrolidinone (VP) was used in the place of HEA in order to increase the hydrophilicity of the polymer. Polymer B was synthesized under free radical conditions using the same monomer ratios as that described for polymer A. The structure of polymer B is shown below.

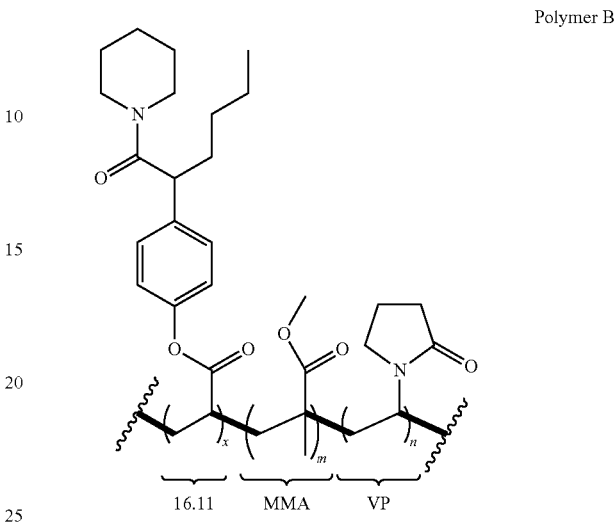

Polymer B 0.5 g of the functional monomer was mixed with 2.0 g of MMA, 1.0 g of vinyl pyrrolidone (VP) and 40 mg of ABCN in 3 ml of DMF and the mixture was degassed by purging with nitrogen for 10 min. Then the mixture was placed into an oil bath thermosetted at 70° C. for 16 hours. Then to the product was added 5 ml of DCM to form a clear solution. The solution was poured into hexane with stirring. The purified product was collected as a white precipitate. The pure product was collected and dried in air at room temperature to afford the title compound as a colourless solid (1.9 g, 54%).

Analysis of the polymer by IR spectroscopy revealed the expected ester carbonyl stretching absorbances at ~1724 $cm^{-1}$ along with the previously assigned piperidine amide carbonyl vibration at ~1640 $cm^{-1}$. The incorporation of VP is evident by IR spectroscopy with a clear absorbance appearing at ~1660 $cm^{-1}$, consistent with the presence of the γ-lactam.

GPC revealed a MW of 5300 Daltons. Finally, the soluble nature of the polymer allowed further analysis by $^1$H NMR spectroscopy. Signals at 6.9-7.2 ppm are assigned to the phenyl moiety of the 16.11 units, whilst the broad peak at 4.0 ppm to 4.3 ppm was assigned to ring methylene adjacent to the N-atom of the pyrrolidinone unit. Large broad signals in the 3.5-3.8 ppm are assigned to the methyl ester of the MMA units (Brar and Kumar, 2002). The signals at 0.9 ppm-2.5 ppm are ascribed to the methylene and methine groups of the polymer backbone and the methylene and methyl groups of side chain of 16.11.

Polymer C

P(TBA-co-MMA-co-VP)

A standard co-polymer (polymer C) was also synthesized where 16.11 was replaced with t-butyl acrylate (TBA). Such a polymer was synthesised in order to ascertain if any background toxicity or anti-settlement activity existed as a function of the copolymer itself.

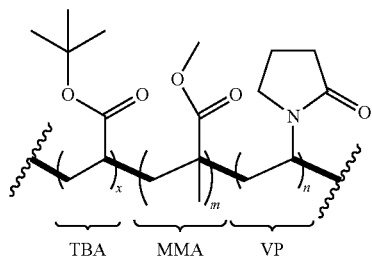

Polymer C

TBA  MMA  VP

The free radical polymerization was carried out using the same mass ratios as for polymers A and B.

0.6 g of tert-butyl acrylate was mixed with 2.0 g of MMA, 1.0 g of vinyl pyrrolidone (VP) and 40 mg of ABCN in 3 ml of DMF and the mixture was degassed by purging with nitrogen for 10 min. Then the mixture was placed into an oil bath thermosetted at 70° C. for 16 hours. Then to the product was added 5 ml of DCM to form a clear solution. The solution was poured into hexane with stirring. The purified product was collected as a white precipitate. The pure product was collected and dried in air at room temperature to afford the desired compound as a colourless solid (3.2 g, 89%)

Analysis of the polymer by IR spectroscopy revealed the presence of key vibrational modes ester and lactam carbonyl groups at 1728 cm$^{-1}$ and 1664 cm$^{-1}$. GPC indicated the desired MW of 67000 Daltons had been achieved and this was much higher than that obtained for polymer B.

$^1$H NMR analysis of the polymer confirmed the presence of the t-butyl moiety in the polymer, appearing at 1.4 ppm.

Examples Part 3—Biological Investigation of Compounds

Methodology

Biological assays were conducted with larval barnacles. Barnacles are dominant and tenacious members of marine fouling communities, and often serve as a substrate for less resistant organisms. Therefore, historically they have been used as a model organism for antifouling studies. To determine the biological response of larvae to test compounds, two bioassays were performed: settlement (using settlement stage cyprids), and toxicity (using nauplii). Procedures followed methods standard in the field, which were first described by Rittschof et al. (1992).

Preparation of Stock Solution for Bioassays

Stock solutions of each compound were made at 50 mg/ml. Pure compounds were diluted in DMSO and sonicated. Stock solutions were stored at 20° C. in 4 ml amber screw cap vials until use. For bioassays, a small amount of stock solution was diluted in 1 µm filtered seawater (in a glass scintillation vial). The solution was then sonicated for 10 minutes. To obtain the desired concentration range, serial dilutions of the test solution were made. As control, a serial dilution of the equivalent amounts of DMSO in seawater was used.

Toxicity Assays

Toxicity assays employed stage II naupliar larvae of the barnacle Amphibalanus amphitrite (previously Balanus amphitrite: Pitombo, 2004). Assay procedures were modified from Rittschof et al. (1992). Adult A. amphitrite were collected from inter-tidal areas near the Kranji mangrove, Singapore. Larval culture was based on Rittschof et al. (1984). Following collection, nauplii were concentrated for use in bioassays by placing a fiber optic light source at one side of the container, and pipetting from the resulting dense cloud of nauplii.

In order to determine LD50 values for each compound, compounds were tested over a range of concentrations between 0-50 µg/ml. For each assay, each compound at each concentration was tested in triplicate with a single batch of nauplii. The overall assay was conducted twice, using two different batches of nauplii. Two controls were run along with each assay (in triplicate): filtered seawater only, and DMSO at 1 µg/ml (since DMSO was used as a solvent for test compounds, this concentration is equivalent to the concentration of DMSO in the highest test compound concentration).

For assays, approximately 20 nauplii (in 50 µl filtered seawater) were added to 1 ml test solution or control, in a 2 ml glass vial (La Pha Pack® PN 11-14-0544). Assays were run for 22-24 hours at 25-27° C. After this time, living and dead nauplii were counted using a Bogorov tray. Nauplii that were approaching death were scored as dead. Data for all assays was combined and LD50 was calculated (where possible) using a probit analysis (Libermann, 1983). If LD50 could not be calculated using probit analysis, values were extrapolated based on plotted data.

Settlement Assays

Settlement assays (using barnacle cyprids) were based on methodology described in Rittschof et al. (1992). Nauplii were cultured as described above, and then reared at 25° C. on an algal mixture of 1:1 v/v of Tetraselmis suecica and Chaetoceros muelleri (approximately density 5×105 cells per ml). Under these conditions, nauplii typically metamorphose to cyprids in 5 days. Cyprids were aged at 4° C. for 2 days. Settlement in filtered seawater controls after aging is generally 45-70%.

Settlement assays were conducted in 7 ml neutral glass vials (Samco® T103/V1; 34×23 mm diameter). For assays, each solution was made at twice the desired final concentration; 0.5 ml of this solution was transferred to vials. To each vial, cyprids were added by transferring 0.5 ml filtered seawater containing 20-40 aged cyprids. As in toxicity assays: each compound at each concentration was run in triplicate with cyprids from a single batch; two controls (filtered seawater and DMSO) were run along with each assays; and the overall assay was conducted twice, using two different batches of cyprids.

Assays were conducted for 24 hours, after which time the number of settled cyprids, the number of free swimming (unsettled) cyprids, and the number of dead cyprids were counted for each vial. Both metamorphosed, juvenile barnacles and cyprids that had committed to settlement (glued themselves to the vial), but had not yet metamorphosed, were counted as 'settled'. Data was expressed as percent settlement. Data for all assays was combined and ED50 (the concentration that caused a 50% reduction in settlement as compared to controls) was calculated (where possible) using a probit analysis (Libermann, 1983). If ED50 could not be calculated using probit analysis, values were extrapolated based on plotted data.

Results

Biological activity for the compounds is shown in Tables 1 and 2. Data is from assays with batches of larvae, and three replicates of each compound per batch. Where $LD_{50}$ or $ED_{50}$ could not be calculated using probit analysis, values were estimated from plotted data. Compounds with a high $LD_{50}$ value (low toxicity), but low $ED_{50}$ (highly potency) are most desirable for anti-fouling purposes. A number of the tested compounds show a therapeutic ratio equal to, or greater than previously identified non-functionalised compounds (12.1 and 12.2; PCT/SG2009/000175)

TABLE 1

Biological activity. $ED_{50}$ values are anti-settlement (tested with barnacle cyprids); $LD_{50}$ values are toxicity (tested with barnacle nauplii).

| Compound | $LD_{50}$ (µg/ml) | $ED_{50}$ (µg/ml) | TR ($LD_{50}/ED_{50}$) |
|---|---|---|---|
| 12.1 (reference) | 9.11 | 1.50 | 6.07 |
| 12.2 (reference) | 9.83 | 2.00 | 4.92 |
| 15.1 | 22.95 | 0.19 | 120.79 |
| 15.2 | >25 | 1.46 | >17.12 |
| 15.3 | 3.67 | 2.85 | 1.29 |
| 15.4 | 8.22 | 3.29 | 2.5 |
| 15.5 | 8.66 | 2.16 | 4.01 |
| 15.6 | 33.21 | 9.12 | 3.64 |
| 15.7 | >25 | 1.75 | 14.29 |
| 16.1 | >50 | 4.11 | >12.17 |
| 16.2 | >50 | 13.4 | >3.73 |
| 16.3 | >50 | 6.35 | >7.87 |
| 16.4 | 27.2 | 0.23 | 118.26 |
| 16.5 | 17.15 | 0.19 | 90.26 |
| 16.6 | >50 | 9.25 | >5.41 |
| 16.7 | 24.58 | 26.88 | 0.91 |
| 16.8 | >50 | 29.05 | 1.72 |
| 16.9 | >50 | >50 | NA |
| 16.10 | >50 | 3.49 | >14.33 |
| 16.11 | 6.57 | 1.53 | 4.29 |

TABLE 2

Biological activity. $ED_{50}$ values are anti-settlement (tested with barnacle cyprids); $LD_{50}$ values are toxicity (tested with barnacle nauplii).

| Compound | $LD_{50}$ (µg/ml) | $ED_{50}$ (µg/ml) | TR ($LD_{50}/ED_{50}$) |
|---|---|---|---|
| 17.1 | 9.27 | 2.37 | 3.91 |
| 17.2 | >50 | 8.69 | >5.75 |
| 17.3 | 18.61 | 2.85 | 6.53 |
| 17.4 | 14.62 | 0.65 | 22.49 |
| 17.5 | 25.14 | 3.44 | 7.31 |
| 17.6 | 9.82 | 2.14 | 4.59 |
| 17.7 | >50 | 34.12 | >1.46 |
| 17.8 | 12.46 | 4.29 | 2.90 |
| 17.9 | >50 | >50 | 1 |

Biological screening therefore indicates that functionalized molecules retained or improve upon desirable biological activity (high potency against barnacle cyprid settlement, yet low toxicity).

Compounds with a high $LD_{50}$ value (low toxicity), but low $ED_{50}$ (highly potency) are most desirable for antifouling purposes. All the compounds gave therapeutic ratios greater than 1.

The above results demonstrate that these new small organic molecules can be used as environmentally benign antifouling additives. These molecules retain effective anti-settlement activity despite differing substituents and substitution patterns on the aromatic ring. Indeed, a number of the compounds display bioactivity comparable to, or better than that of the unsubstituted parent structure. These new molecules improve upon the parent structure in that they can support functionality which can be used to tether or anchor the antifouling compounds to a marine coating system.

The compounds can be blended into existing acrylate paints and are therefore practical alternatives to the current coating options. Furthermore, due to their simple structure the compounds are attractive candidates for degradation via bacterial means in the marine environment and are less likely to accumulate and pose a health risk in the future. In addition, given that existing organic biocides such as Diuroh® and Sea-Nine® have been shown to bioaccumulate and cause detrimental effects in the marine environment, the compounds of the present invention represent a valuable alternative to traditional metal-based additives.

Examples Part 4—Polymeric Systems

Release Studies
Preparation of Multiwell Plates for Laboratory Assays

Two batches of polystyrene 4×6 multiwell plates (base of the well 2 cm$^2$) were prepared for laboratory assays. A stock solution of polymer was made by dissolving 50 mg of P(MMA-co-16.11-co-VP) in 1.0 ml of ethanol. The plates were coated with the desired amount of the stock solution (10 µl, 20 µl, 30 µl, 40 µl, 50 µl, and 70 µl) and placed in air at 27° C. for 6 hours. Then deionised water was added into those wells. After 24 hours the water was removed completely from the wells and stored for further analysis. The polystyrene plates were then dried under a stream of dry air. Meanwhile, the control specimens were prepared in the same way without water soaking.

Settlement Assay

The coatings were tested for antifouling effects using barnacle cyprid settlement assays. Cyprids were cultured as described above. After 5 days, cyprids were obtained and they were aged at 4° C. for 2 days before the settlement experiment. For experiment, cyprids were added by transferring 1 ml filtered seawater containing 20-40 aged cyprids into each well. The multi-well plates were incubated for 24 hours, after which time the number of settled cyprids, the number of free swimming (unsettled) cyprids, and the number of dead cyprids were counted for each well.

The result of the assay is given in FIG. 1. For all treatments, cyprid mortality was less than 10%. Settlement on the control coating, P(MMA-co-tBA-co-VP), was similar to that for uncoated polystyrene. Wells coated with P(MMA-co-16.11-co-VP) showed reduction in cyprid settlement, with no settlement observed for treatments >40 µl.

Quantification by HPLC

Aliquots of solutions obtained after soaking for 24 hours were mixed with a known volume of the internal standard and directly injected into a HPLC system and monitored at 226 nm. The amount of 16.5 released into the solutions obtained after soaking are shown below in Table 3 along with the calculated release rate. In each case, the amount of 16.5 released falls in a very narrow range (0.15-0.45 µg), representing the similar surface area exposed to the aqueous environment in each case, regardless of the quantity of polymer.

TABLE 3

Mass released and calculated release rates of 16.5 released from coated wells after 24 hours.

| Volume of P(MMA-co-16.11-co-VP) stock solution | Mass of P(MMA-co-16.11-co-VP) | Released 16.5 (µg) | Release Rate (µg cm$^2$ day$^{-1}$) |
|---|---|---|---|
| 10 µL | 500 µg | 0.247 | 0.124 |
| 20 µL | 1000 µg | 0.136 | 0.0677 |
| 30 µL | 1500 µg | 0.212 | 0.106 |
| 40 µL | 2000 µg | 0.400 | 0.200 |

TABLE 3-continued

Mass released and calculated release rates of 16.5 released from coated wells after 24 hours.

| Volume of P(MMA-co-16.11-co-VP) stock solution | Mass of P(MMA-co-16.11-co-VP) | Released 16.5 (µg) | Release Rate (µg cm² day⁻¹) |
|---|---|---|---|
| 50 µL | 2500 µg | 0.242 | 0.121 |
| 70 µL | 3500 µg | 0.430 | 0.215 |

FIG. 1 shows average percentage settlement of barnacles in the coated wells. P(MMA-co-tBA-co-VP) was applied as the control coating. Settlement on this coating was similar to that for uncoated polystyrene. Increased amounts of P(MMA-co-16.11-co-VP) resulted in decline in barnacle settlement, with no settlement for test treatments >40 µl. In all treatments, cyprid mortality was less than 10%.

Following successful release of active compound 16.5 from the polymer, analysis was carried out into the hydrolysis of compound 16.11 from the polymer to release compound 16.5 into solution.

Preparation of Coated Vials for Laboratory Analysis

The inner base of glass vials with an internal diameter of 12 mm was matted with coarse sandpaper and then inoculated with a stock solution of P(MMA-co-16.11-co-VP) in ethanol such that the quantity of copolymer present is 500 µg and 2500 µg of P(MMA-co-16.11-co-VP) respectively, covering a surface area of 1.13 cm². The vials were allowed to cure overnight prior to the addition of 2 mL of deionised water was added to each well. After 24 hours, the water was removed and replaced by 2 mL of fresh deionised water. The process was repeated after a further 24 hours and again for a further 48 hours giving a time course of 1, 2 and 4 days. Aliquots of the collected solutions were run against an internal standard (phenol), monitoring the response ratio at 226 nm. The resulting mass of 16.5 released at the specified time points are shown in Table 4.

In each case the presence of 16.5 in the water was confirmed by analysis of the aliquots by analytical HPLC-ESI.

TABLE 4

Mass of 16.5 released from polymer coated vials after 24 hours

| Mass of P(MMA-co-16.11-co-VP) coating | Mass of 16.5 released (µg) | | | |
|---|---|---|---|---|
| | Day 1 | Day 2 | Day 3-4 | Day 5-7 |
| 500 µg | 0.482 | 0.0064 | 0.046 | 0.0054 |
| | 0.572 | 0.0022 | 0.039 | 0.0086 |
| | 0.534 | 0.0018 | 0.083 | 0.0096 |
| 2500 µg | 0.067 | 0.0042 | 0.0031 | 0.0263 |
| | 0.034 | 0.0051 | 0.0013 | 0.0233 |
| | 0.050 | 0.0091 | 0.0053 | 0.0350 |

The average release rates for the first four days are shown in Table 5. The strikingly different release rates of the 500 µg and 2500 µg coated vials on day 1 (0.468 µg cm² day⁻¹ and 0.045 µg cm² day⁻¹ respectively) reflect the different surface roughness of the coatings at the start of the release studies. After day 1 it can be seen that the release rates converge and this level of release is sustained at similar levels over the next 6 days.

TABLE 5

Release rate of 16.5 from P(MMA-co-16.11-co-VP) coated vials as a function of time.

| Mass of P(MMA-co-16.11-co-VP) Coating | Average release rate of 16.5 (µg cm⁻² day⁻¹) | | | |
|---|---|---|---|---|
| | Day 1 | Day 2 | Day 4 | Day 7 |
| 500 µg | 0.482 | 0.0031 | 0.0089 | 0.0049 |
| 2500 µg | 0.0448 | 0.0054 | 0.0031 | 0.0083 |

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Armarego, W. L. F.; C. L. L. Chai. 2003. Purification of Laboratory Chemicals; 5th ed.; Butterwortth-Heinemann: Sydney.

Brar, A. S. and R. Kumar. 'Investigation of Microstructure of the N-Vinyl-2-pyrrolidone/Methyl Methacrylate Copolymers by NMR Spectroscopy' Inc. J Appl Polym Sci 85: 1328-1336, 2002.

Libermann H. R. 'Estimating $LD_{50}$ using the probit technique: a basic computer program' Drug Chem. Toxicol 1983, 6, 111-116.

Pitombo F. B. 2004. Phylogenetic analysis of the Balanidae (Cirripedia, Balanomorpha). Zool. Scr. 33: 261-276.

Rittschof D.; Clare, A. S.; Gerhart, D. J.; Avelin, M. Sr.; Bonaventura, J. 'Barnacle in-vitro assays for biologically active substances: toxicity and settlement inhibition assays using mass cultured Balanus amphitrite amphitrite Darwin' Biofouling 1992, 6, 115-122.

Rittschof D.; Branscomb, E.; Costlow, J. 'Settlement and behavior in relation to flow and surface in larval barnacles, Balanus amphitrite Darwin' J. Exp. Mar. Biol. Ecol. 1984, 82, 131-146.

Teo, L. M. S., D. Rittschof, F. Jameson, C. Chai, C. L. Chen, S. C. Lee. Antifouling compounds for use in marine environment. PCT Int. Appl. (2009), WO2009139729 A1.

Voulvoulis, N. 'Antifouling paint booster biocides: occurrence and partitioning in water and sediments' In: Konstantinou, I. K. (ed). Antifouling Paint Biocides. The Handbook of Environmental Chemistry, 2006, Volume 5, Part O, pp. 155-170. Springer-Verlag Berlin-Heidelberg.

The invention claimed is:

1. A compound of formula (I) or a salt thereof:

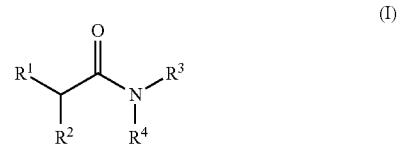

(I)

wherein

R¹ is saturated $C_3$ to $C_{12}$ alkyl or $C_3$ to $C_{12}$ alkenyl;

R² is

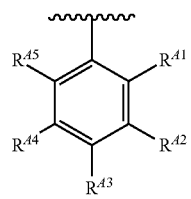

(Ia)

wherein each of $R^{A1}$, $R^{A2}$, $R^{A3}$, $R^{A4}$ and $R^{A5}$ is independently selected from OH, $R^{S1}$OH, $OR^{S2}$, $R^{S1}OR^{S2}$, OC(O)H, OC(O)$R^{S2}$, $R^{S1}$OC(O)H, $R^{S1}$OC(O)$R^{S2}$, C(O)OH, C(O)$OR^{S2}$, $R^{S1}$C(O)OH, $R^{S1}$C(O)$OR^{S2}$, $OR^{S1}$OH, $OR^{S1}OR^{S2}$, $OR^{S1}$OC(O)H, $OR^{S1}$OC(O)$R^{S2}$, $OR^{S1}$C(O)OH, $OR^{S1}$C(O)$OR^2$, H and $R^{S2}$, wherein, if present, each $R^{S1}$ is independently optionally substituted $C_1$ to $C_5$ alkylene, and wherein, if present, each $R^{S2}$ is independently selected from optionally substituted $C_1$ to $C_5$ alkyl, $C_2$ to $C_5$ alkenyl and $C_1$ to $C_5$ alkylsilyl-$C_1$ to $C_5$ alkylene, with the proviso that at least one of $R^{A1}$, $R^{A2}$, $R^{A3}$, $R^{A4}$ and $R^{A5}$ is not H or $R^{S2}$, and each of R³ and R⁴ is Me.

2. The compound according to claim 1 wherein R¹ is $C_4$ alkyl or $C_6$ alkyl.

3. The compound according to claim 1, wherein, if present, each $R^{S1}$ is independently optionally substituted $C_1$ to $C_3$ alkylene, and wherein, if present, each $R^{S2}$ is independently selected from optionally substituted $C_1$ to $C_3$ alkyl and $C_2$ to $C_3$ alkenyl and $C_1$ to $C_3$ alkylsilyl-$C_1$ to $C_3$ alkylene.

4. The compound according to claim 1, wherein

R² is

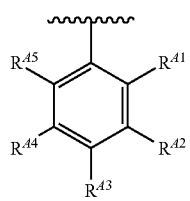

wherein each of $R^{A1}$, $R^{A2}$, $R^{A3}$, $R^{A4}$ and $R^{A5}$ is independently selected from OH, OMe, C(O)OH, $CH_2OH$, $CH_2OAc$, $OC(O)CH_3$, $OCH_2C(O)OH$, $OCH_2C(O)OCH_3$, $OCH_2CH_2OH$, $OCH_2CH_2OC(O)CH_3$, $OCH_2CH_2Si(Me)_3$ and $OC(O)CH=CH_2$, and H, with the proviso that at least one of $R^{A1}$, $R^{A2}$, $R^{A3}$, $R^{A4}$ and $R^{A5}$ is not H.

5. The compound according to claim 4, wherein at least two of $R^{A1}$, $R^{A2}$, $R^{A3}$, $R^{A4}$ and $R^{A5}$ are H.

6. A compound according to claim 5, wherein at least three of $R^{A1}$, $R^{A2}$, $R^{A3}$, $R^{A4}$ and $R^{A5}$ are H.

7. The compound according to claim 1, wherein the compound is selected from compounds

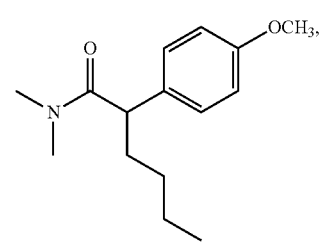

17.2

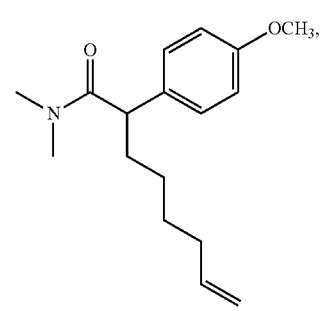

17.3

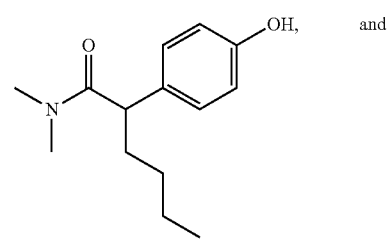

17.7 and

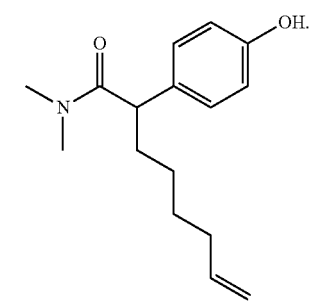

17.8

8. A method of reducing or preventing fouling of a substrate comprising the step of applying to the substrate a compound according to claim 1.

9. The method according to claim 8, wherein R¹ is $C_4$ alkyl or $C_6$ alkyl.

10. The method according to claim 8, wherein, if present, each $R^{S1}$ is independently optionally substituted $C_1$ to $C_3$ alkylene, and wherein, if present, each $R^{S2}$ is independently selected from optionally substituted $C_1$ to $C_3$ alkyl and $C_2$ to $C_3$ alkenyl and $C_1$ to $C_3$ alkylsilyl-$C_1$ to $C_3$ alkylene.

11. The method according to claim 8, wherein the compound is selected from

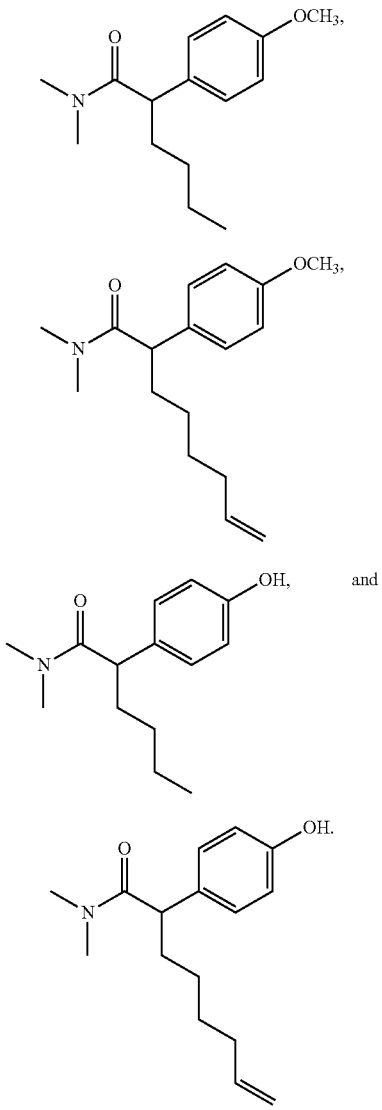

17.2

17.3

17.7 and 17.8

12. A polymer comprising at least one repeating unit formed from a compound of formula (I) as defined in claim 1.

13. The polymer according to claim 12, wherein the polymer is selected from a (meth)acrylate polymer and a silicone polymer.

14. The polymer according to claim 13, wherein the polymer is a (meth)acrylate polymer and comprises repeating units derived from one or more of methylmethacrylate (MMA), hydroxyethyl acrylate (HEA) and vinyl pyrrolidinone (VP).

15. The polymer according to claim 12 comprising a pendant group according to formula X

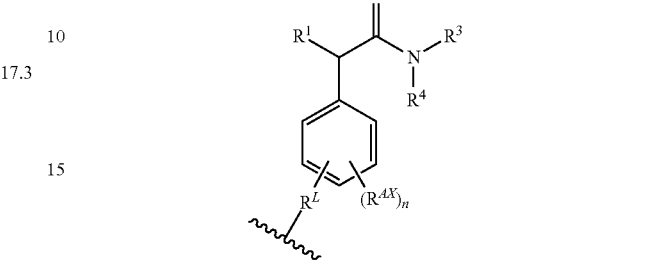

(X)

wherein
$R^1$ is saturated $C_3$ to $C_{12}$ alkyl or $C_3$ to $C_{12}$ alkenyl;
each of $R^3$ and $R^4$ is Me,
each $R^{AX}$ is independently selected from OH, $R^{S1}$OH, $OR^{S2}$, $R^{S1}OR^{S2}$, OC(O)H, OC(O)$R^{S2}$, $R^{S1}$OC(O)H, $R^{S1}$OC(O)$R^{S2}$, C(O)OH, C(O)$OR^{S2}$, $R^{S1}$C(O)OH, $R^{S1}$C(O)$OR^{S2}$, $OR^{S1}$OH, $OR^{S1}OR^{S2}$, $OR^{S1}$OC(O)H, $OR^{S1}$OC(O)$R^{S2}$, $OR^{S1}$C(O)OH, $OR^{S1}$C(O)$OR^{S2}$, H and $R^{S2}$,
n is an integer in the range 0 to 4,
and wherein
$R^L$ is a linker group selected from —O—, $R^{L1}$O, $OR^{L2}$, $R^{L1}OR^{L2}$, OC(O), OC(O)$R^{L2}$, $R^{L1}$OC(O), $R^{L1}$OC(O)$R^{L2}$, C(O)O, C(O)$OR^{L2}$, $R^{L1}$C(O)O, $R^{L1}$C(O)$OR^{L2}$, $OR^{L1}$O, $OR^{L1}OR^{L2}$, $OR^{L1}$OC(O), $OR^{L1}$OC(O)$R^{L2}$, $OR^{L1}$C(O)O and $OR^{L1}$C(O)$OR^{L2}$;
wherein, if present, each $R^{L1}$ is independently optionally substituted $C_1$ to $C_5$ alkylene, and
wherein, if present, each $R^{L2}$ is independently optionally substituted $C_1$ to $C_5$ alkylene.

16. An antifouling coating composition comprising a compound of formula (I) as defined in claim 1 or a polymer according to claim 12.

17. A method of reducing or preventing fouling of a substrate, which method comprises the step of applying to the substrate a polymer according to claim 12 or coating composition according to claim 16.

18. The method according to claim 17, wherein the method of reducing or preventing fouling is a method of reducing or preventing biofilm formation by one or more of bacteria, fungi, algae and protozoans.

19. The method according to claim 8, wherein the method reduces or prevents biofilm formation by one or more of bacteria, fungi, algae and protozoans.

\* \* \* \* \*